(12) United States Patent
Gopu et al.

(10) Patent No.: US 12,165,745 B2
(45) Date of Patent: Dec. 10, 2024

(54) BIOMARKERS FOR AGE

(71) Applicant: Viome Life Sciences, Inc., Bellevue, WA (US)

(72) Inventors: Vishakh Gopu, Wakefield, RI (US); Ying Cai, Queens, NY (US); Hal Tily, New York, NY (US); Guruduth S. Banavar, Pelham Manor, NY (US); Momchilo Vuyisich, Bothell, WA (US)

(73) Assignee: Viome Life Sciences, Inc., Bellevue, WA (US)

( * ) Notice: Subject to any disclaimer, the term of this patent is extended or adjusted under 35 U.S.C. 154(b) by 0 days.

(21) Appl. No.: 17/855,646

(22) Filed: Jun. 30, 2022

(65) Prior Publication Data
US 2022/0344003 A1    Oct. 27, 2022

Related U.S. Application Data

(63) Continuation of application No. PCT/US2021/049187, filed on Sep. 6, 2021.

(60) Provisional application No. 63/075,072, filed on Sep. 4, 2020.

(51) Int. Cl.
G16B 25/10 (2019.01)
C12Q 1/689 (2018.01)
G16B 30/10 (2019.01)
G16B 40/20 (2019.01)

(52) U.S. Cl.
CPC ............. *G16B 25/10* (2019.02); *C12Q 1/689* (2013.01); *G16B 30/10* (2019.02); *G16B 40/20* (2019.02)

(58) Field of Classification Search
CPC ........ G16B 25/10; G16B 30/10; G16B 40/20; C12Q 1/689
See application file for complete search history.

(56) References Cited

U.S. PATENT DOCUMENTS

2019/0032139 A1    1/2019   Zhang et al.

FOREIGN PATENT DOCUMENTS

| WO | 2016141330 A1 | 9/2016 |
| WO | 2018160899 A1 | 9/2018 |
| WO | 2018170289 A1 | 9/2018 |
| WO | 2020084536 A1 | 4/2020 |
| WO | 2022051700 A1 | 3/2022 |

OTHER PUBLICATIONS

Proctor, L.M. et al. Nature 569:641. May 2019. (Year: 2019).*
Morgan, X.C. Genome Biology 13:R79. (Year: 2012).*
Duan et al. "Age-related changes in microbial composition and function in cynomolgus macaques," Aging. Dec. 14, 2019, vol. 11, No. 24, p. 12080-12096.
International Search Report and Written Opinion for PCT/US21/49187, dated Feb. 2, 2022, 17 pages.

* cited by examiner

*Primary Examiner* — Diana B Johannsen
(74) *Attorney, Agent, or Firm* — Morgan, Lewis & Bockius LLP

(57) ABSTRACT

Provided herein are methods and systems for inferring biological age in a subject. The methods involve analyzing data from a microbiome and/or somatic cell transcriptome from a subject and executing a model that infers biological age.

18 Claims, 25 Drawing Sheets

FIG. 1A

| Feature | Feature type | KO name/taxa genus | KO Definition | Coefficient |
|---|---|---|---|---|
| Streptococcus gordonii | taxa | Streptococcus | | 1.096848064 |
| Propionibacterium acidifaciens | taxa | Propionibacterium | | 0.898507872 |
| Streptococcus mutans | taxa | Streptococcus | | 0.875641544 |
| Olsenella profusa | taxa | Olsenella | | 0.732465127 |
| Streptococcus vestibularis | taxa | Streptococcus | | 0.678402771 |
| Alloscardovia omnicolens | taxa | Alloscardovia | | 0.675622463 |
| Clostridium phoceensis | taxa | Clostridium | | 0.604504365 |
| Massilioclostridium coli | taxa | Massilioclostridium | | 0.568933874 |
| Ruminococcaceae bacterium Marseille-P2963 | taxa | Ruminococcaceae | | 0.563122972 |
| Bifidobacterium dentium | taxa | Bifidobacterium | | 0.527505664 |
| Ruminococcus gauvreauii | taxa | Ruminococcus | | 0.499503648 |
| Roseburia intestinalis | taxa | Roseburia | | 0.483384645 |
| Streptococcus sp. HMSC10A01 | taxa | Streptococcus | | 0.472488487 |
| Ruminococcus sp. AT10 | taxa | Ruminococcus | | 0.461622168 |
| Veillonella atypica | taxa | Veillonella | | 0.460069606 |
| Turicibacter sp. HGF1 | taxa | Turicibacter | | 0.45721501 |
| Olsenella uli | taxa | Olsenella | | 0.451591839 |
| Penicillium digitatum | taxa | Penicillium | | 0.448122934 |
| Pseudomonas aeruginosa | taxa | Pseudomonas | | 0.441234121 |
| Intestinimonas butyriciproducens | taxa | Intestinimonas | | 0.432166631 |
| Ruminococcus sp. Marseille-P3213 | taxa | Ruminococcus | | 0.400291721 |
| Streptococcus sp. CCH8-G7 | taxa | Streptococcus | | 0.399236006 |
| Lachnospiraceae bacterium TF01-11 | taxa | Lachnospiraceae | | 0.382550408 |
| Bifidobacterium sp. MSTE12 | taxa | Bifidobacterium | | 0.350195108 |

FIG. 1B

| Feature | Feature type | KO name/taxa genus | KO Definition | Coefficient |
|---|---|---|---|---|
| Pseudoflavonifractor capillosus | taxa | Pseudoflavonifractor | | 0.348449174 |
| Streptococcus parasanguinis | taxa | Streptococcus | | 0.339412958 |
| Clostridia bacterium UC5 1-1E11 | taxa | Clostridia | | 0.339252836 |
| K00366 | ko | nirA | ferredoxin-nitrite reductase | 0.336961427 |
| Subdoligranulum sp 4_3_54A2FAA | taxa | Subdoligranulum | | 0.335526378 |
| Corynebacterium matruchotii | taxa | Corynebacterium | | 0.335138088 |
| Actinomyces dentalis | taxa | Actinomyces | | 0.333274493 |
| Actinomycetaceae bacterium BA112 | taxa | Actinomycetaceae | | 0.323728696 |
| Bacteroides sp. HPS0048 | taxa | Bacteroides | | 0.319512439 |
| Butyricicoccus pullicaecorum | taxa | Butyricicoccus | | 0.313530323 |
| K02198 | ko | ccmF | cytochrome c-type biogenesis protein C | 0.3081490335 |
| Rothia mucilaginosa | taxa | Rothia | | 0.30571846 |

FIG. 1C

| Feature | Feature type | KO name/taxa genus | KO Definition | Coefficient |
|---|---|---|---|---|
| Parascardovia denticolens | taxa | Parascardovia | | 0.30563163 |
| K04835 | ko | mal | methylaspartate ammonia-lyase | 0.293778326 |
| K13652 | ko | K13652 | AraC family transcriptional regulator | 0.237558869 |
| K02968 | ko | RP-S20, rpsT | small subunit ribosomal protein S20 | 0.224043154 |
| K10254 | ko | ohyA, sph | oleate hydratase | 0.203779832 |
| K02959 | ko | RP-S16, MRPS16, rpsP | small subunit ribosomal protein S16 | 0.188542109 |
| K01156 | ko | Res | type III restriction enzyme | 0.179655447 |
| K01668 | ko | E4 1.99.2 | tyrosine phenol-lyase | 0.179619896 |
| K02884 | ko | RP-L19, MRPL19, rplS | large subunit ribosomal protein L19 | 0.176382562 |
| K12452 | ko | ascC, ddhC, rfbH | CDP-4-dehydro-6-deoxyglucose reduct | 0.17508616 |
| K03386 | ko | PRDX2_4, ahpC | peroxiredoxin 2/4 | 0.171699871 |
| K03476 | ko | ulaG | L-ascorbate 6-phosphate lactonase | 0.169250198 |
| K04047 | ko | dps | starvation-inducible DNA-binding protein | 0.166712651 |
| K06012 | ko | gpr | spore protease | 0.165579178 |
| K07154 | ko | hipA | serine/threonine-protein kinase HipA | 0.164302858 |
| K04480 | ko | mtaB | methanol--5-hydroxybenzimidazolylcob | 0.164237245 |
| K04940 | ko | odh | opine dehydrogenase | 0.160266448 |
| K04758 | ko | feoA | ferrous iron transport protein A | 0.159558968 |
| K05349 | ko | bglX | beta-glucosidase | 0.153226625 |
| K04081 | ko | ibpB | molecular chaperone IbpB | 0.152901292 |
| K00287 | ko | DHFR, folA | dihydrofolate reductase | 0.151816099 |

FIG. 1D

| Feature | Feature type | KO name/taxa genus | KO Definition | Coefficient |
|---|---|---|---|---|
| K00112 | ko | glpB | glycerol-3-phosphate dehydrogenase sub | 0.150194208 |
| K07659 | ko | ompR | two-component system, OmpR family | -0.150312632 |
| K07493 | ko | K07493 | putative transposase | -0.156278321 |
| K10708 | ko | frlB | fructoselysine 6-phosphate deglycase | -0.170403664 |
| K01966 | ko | PCCB, pccB | propionyl CoA carboxylase beta chain | -0.171672389 |
| K03286 | ko | TC.OOP | OmpA-OmpF porin, OOP family | -0.17506573 |
| K02109 | ko | ATPF0B, atpF | F-type H+ transporting ATPase subunit | -0.17563172 |
| K02016 | ko | ABC.FEV.S | iron complex transport system substrate | -0.175726058 |
| K07071 | ko | K07071 | uncharacterized protein | -0.176085743 |
| K05770 | ko | TSPO, BZRP | translocator protein | -0.176858022 |
| K07813 | ko | agrB | accessory gene regulator B | -0.178838044 |
| K03088 | ko | rpoE | RNA polymerase sigma 70 factor, ECF | -0.179307037 |
| K07307 | ko | dmsB | anaerobic dimethyl sulfoxide reductase | -0.182090537 |
| K02003 | ko | ABC.CD.A. | putative ABC transport system ATP-bind | -0.191668065 |
| K07118 | ko | K07118 | uncharacterized protein | -0.196733439 |
| K10796 | ko | prdE | D-proline reductase (dithiol) stabilizing p | -0.203406148 |
| K10709 | ko | frlC | fructoselysine 4-epimerase | -0.214102024 |
| K06405 | ko | SpoVAC | stage V sporulation protein AC | -0.214298678 |
| K00265 | ko | gltB | glutamate synthase (NADPH) large chain | -0.237766729 |
| K00033 | ko | PGD, gnd, gntZ | 6-phosphogluconate dehydrogenase | -0.244258506 |
| K01023 | ko | assT | aryl-sulfate sulfotransferase | -0.252036979 |
| K02190 | ko | cbiK | sirohydrochlorin cobaltochelatase | -0.262427383 |
| K04564 | ko | SOD2 | superoxide dismutase, Fe-Mn family | -0.269714807 |

FIG. 1E

| Feature | Feature type | KO name/taxa genus | KO Definition | Coefficient |
|---|---|---|---|---|
| K01580 | ko | E4.1.1.15, gadB, gadA, GAD | glutamate decarboxylase | -0.296086124 |
| Dialister invisus | taxa | Dialister | | -0.307302019 |
| Faecalibacterium prausnitzii | taxa | Faecalibacterium | | -0.308762608 |
| Tobacco mild green mosaic virus | taxa | Tobacco | | -0.310913864 |
| K02112 | ko | ATPF1B, atpD | F-type H+/Na+ transporting ATPase sub | -0.311481231 |
| Peptostreptococcus stomatis | taxa | Peptostreptococcus | | -0.314850809 |
| Atopobium sp. HMSC064B08 | taxa | Atopobium | | -0.315672391 |
| Clostridiales bacterium | taxa | Clostridiales | | -0.324040355 |
| Ruminococcus faecis | taxa | Ruminococcus | | -0.326587317 |
| K10355 | ko | ACTF | actin, other eukaryote | -0.335655745 |
| Atopobium rimae | taxa | Atopobium | | -0.336542388 |
| Actinomyces sp. oral taxon 181 | taxa | Actinomyces | | -0.341309072 |
| K07171 | ko | mazF, ndoA, chpA | mRNA interferase MazF | -0.343614885 |
| Streptococcus intermedius | taxa | Streptococcus | | -0.347396224 |
| Parasutterella excrementihominis | taxa | Parasutterella | | -0.349866573 |
| Clostridiales bacterium VE202.26 | taxa | Clostridiales | | -0.356383705 |
| Sutterella wadsworthensis | taxa | Sutterella | | -0.356847354 |
| Clostridiales bacterium VE202.21 | taxa | Clostridiales | | -0.377044633 |
| Lactobacillus iners | taxa | Lactobacillus | | -0.38034029 |
| Urmitella tinonensis | taxa | Urmitella | | -0.384563 |
| Abiotrophia sp. HMSC24B09 | taxa | Abiotrophia sp. | | -0.386345612 |
| Hungatella hathewayi | taxa | Hungatella | | -0.405268482 |
| K13993 | ko | HSP20 | HSP20 family protein | -0.432781321 |

FIG. 1F

| Feature | Feature type | KO name/taxa genus | KO Definition | Coefficient |
|---|---|---|---|---|
| Ruminococcus sp. DSM 100440 | taxa | Ruminococcus | | -0.446498565 |
| Clostridiales bacterium VE202-03 | taxa | Clostridiales | | -0.464765001 |
| Streptococcus sp. F0442 | taxa | Streptococcus | | -0.468220928 |
| Coprococcus eutactus | taxa | Coprococcus | | -0.473524888 |
| Haemophilus sputorum | taxa | Haemophilus | | -0.476365458 |
| Actinomyces gerencseriae | taxa | Actinomyces | | -0.476781688 |
| Catabacter hongkongensis | taxa | Catabacter | | -0.505380204 |
| Gemella morbillorum | taxa | Gemella | | -0.513861439 |
| Clostridium ventriculi | taxa | Clostridium | | -0.560181302 |
| Eubacterium sp. 3_1_31 | taxa | Eubacterium | | -0.575998864 |
| Lactobacillus crispatus | taxa | Lactobacillus | | -0.578705498 |
| Bifidobacterium longum | taxa | Bifidobacterium | | -0.589850282 |
| Campylobacter hominis | taxa | Campylobacter | | -0.604874779 |
| Streptococcus anginosus | taxa | Streptococcus | | -0.628738212 |
| Shewanella colwelliana | taxa | Shewanella | | -0.635889952 |
| Staphylococcus aureus | taxa | Staphylococcus | | -0.647673897 |
| Haemophilus pittmaniae | taxa | Haemophilus | | -0.706798371 |
| Romboutsia timonensis | taxa | Romboutsia | | -0.724912035 |
| Turicibacter sanguinis | taxa | Turicibacter | | -0.751816485 |
| Turicibacter sp. H121 | taxa | Turicibacter | | -0.815848332 |

FIG. 2A

| gene_id | Gene Symbol | Mean coefficient | S.D coefficient | Absolute value of mean |
|---|---|---|---|---|
| ENSG00000182463 | TSHZ2 | 1.498428014950120 | 0.072685154251949 | 1.498428014950120 |
| ENSG00000146674 | IGFBP3 | 0.627002139446755 | 0.124086552563709 | 0.627002139446755 |
| ENSG00000188462 | NAP1L2 | 0.606523540528440 | 0.080797424872106 | 0.606523540528440 |
| ENSG00000150782 | IL18 | 0.456424078078881 | 0.146380197692384 | 0.456424078078881 |
| ENSG00000138640 | FAM13A | 0.394436663226848 | 0.097917815840277 | 0.394436663226848 |
| ENSG00000171791 | BCL2 | 0.374769717960998 | 0.116077886617134 | 0.374769717960998 |
| ENSG00000180875 | GREM2 | 0.366441883727407 | 0.066319737301010 | 0.366441883727407 |
| ENSG00000166395 | SDRCS3 | 0.359419162787531 | 0.127084403108532 | 0.359419162787531 |
| ENSG00000123358 | NR4A1 | 0.344548599179320 | 0.073437104457937 | 0.344548599179320 |
| ENSG00000154734 | ADAMTS1 | 0.329846526243995 | 0.136136971757898 | 0.329846526243995 |
| ENSG00000158813 | EDA | 0.319892046721411 | 0.104157162032032 | 0.319892046721411 |
| ENSG00000107317 | PTGDS | 0.296427073528512 | 0.133038866376342 | 0.296427073528512 |
| ENSG00000129538 | RNASE1 | 0.295291578542884 | 0.114138795311820 | 0.295291578542884 |
| ENSG00000174138 | RGMB | 0.295233092873817 | 0.086867722165905 | 0.295233092873817 |
| ENSG00000134429 | POF1B | 0.295031429867982 | 0.084913081351207 | 0.295031429867982 |
| ENSG00000135384 | PTGFR2 | 0.292391418710273 | 0.122653190554766 | 0.292391418710273 |
| ENSG00000154917 | RAB6B | 0.291462085267937 | 0.083048625297159 | 0.291462085267937 |
| ENSG00000128656 | CHN1 | 0.289759453091434 | 0.118036092975508 | 0.289759453091434 |
| ENSG00000074416 | MGLL | 0.287589365170416 | 0.055911807294920 | 0.287589365170416 |
| ENSG00000146385 | TAAR8 | 0.286953428332127 | 0.165689888864711 | 0.286953428332127 |
| ENSG00000189283 | FHIT | 0.286894916635105 | 0.111977822831883 | 0.286894916635105 |
| ENSG00000101230 | ISM1 | 0.286345893172852 | 0.087618349383014 | 0.286345893172852 |
| ENSG00000109452 | INPP4B | 0.263416673988639 | 0.083292274763913 | 0.263416673988639 |
| ENSG00000181847 | TIGIT | 0.224028303222596 | 0.085347267711574 | 0.224028303222596 |
| ENSG00000198832 | SELENOM | 0.243897563851951 | 0.064647213330303 | 0.243897563851951 |
| ENSG00000105664 | COMP | 0.242266630015472 | 0.014680301740048 | 0.242266630015472 |
| ENSG00000254122 | PCDHGB7 | 0.239497377099586 | 0.072679819577532 | 0.239497377099586 |
| ENSG00000120833 | SOCS2 | 0.236968649397088 | 0.047267070374675 | 0.236968649397088 |
| ENSG00000185090 | MANEAL | 0.233569823863271 | 0.117194891903674 | 0.233569823863271 |
| ENSG00000146530 | VWDE | 0.227293780364277 | 0.080075992033258 | 0.227293780364277 |
| ENSG00000198746 | GPATCH3 | 0.220172605948421 | 0.119134263820453 | 0.220172605948421 |

FIG. 2B

| gene_id | Gene Symbol | Mean coefficient | S.D coefficient | Absolute value of mean |
|---|---|---|---|---|
| ENSG00000185518 | SV2B | 0.217641880132357657 | 0.048000097789403566 | 0.217641880133257657 |
| ENSG00000099822 | HCN2 | 0.215180412617513920 | 0.218941200583337524 | 0.215180412617513920 |
| ENSG00000182366 | PDZK1IP1 | 0.213107043325519936 | 0.108916292039865937 | 0.213107043325519936 |
| ENSG00000203797 | DDO | 0.210854446867973865 | 0.133144042676766833 | 0.210854446867973865 |
| ENSG00000137310 | TCF19 | 0.209751306710211 | 0.120903366443389173 | 0.209751306710211 |
| ENSG00000013573 | DDX11 | 0.206982755353630151 | 0.109603576468243324 | 0.206982755353630151 |
| ENSG00000120262 | CCDC170 | 0.206486677643866467 | 0.114653724118069359 | 0.206486677643866467 |
| ENSG00000113812 | ACTR8 | 0.204878449598981637 | 0.148812805080478 | 0.204878449598981637 |
| ENSG00000100346 | CACNA1I | 0.199114388317712308 | 0.115587088674166885 | 0.199114388317712308 |
| ENSG00000124788 | ATXN1 | 0.198084815665234568 | 0.087342972146293815 | 0.198084815665234568 |
| ENSG00000163071 | SPATA18 | 0.196928255294957860 | 0.107223760562960096 | 0.196928255294957860 |
| ENSG00000188184 | PCDH18 | 0.196903112502229178 | 0.105410541777022291 | 0.196903112502229178 |
| ENSG00000135726 | CD70 | 0.191343962300057398 | 0.109425115546613456 | 0.191343962300057398 |
| ENSG00000189367 | KIAA0408 | 0.187757221299997527 | 0.061072006222639114 | 0.187757221299997527 |
| ENSG00000178199 | ZC3H12D | 0.183302029364416284 | 0.028479655308598068 | 0.183302029364416284 |
| ENSG00000179934 | CCR8 | 0.180644140025525258 | 0.113805130227436197 | 0.180644140025525258 |
| ENSG00000114737 | CISH | 0.175651651693334432 | 0.122460297002585873 | 0.175651651693334432 |
| ENSG00000152556 | PFKM | 0.173627531163817 | 0.104484891748754386 | 0.173627531163817 |
| ENSG00000147676 | MAL2 | 0.172095423108282303 | 0.111831854928484849 | 0.172095423108282303 |
| ENSG00000143851 | PTPN7 | 0.171767122613333194 | 0.107867207690296380 | 0.171767122613333194 |
| ENSG00000137672 | TRPC6 | 0.171390777500015970 | 0.100310422074626072 | 0.171390777500015970 |
| ENSG00000156049 | GNA14 | 0.170581591219841400 | 0.096661512131707290 | 0.170581591219841400 |
| ENSG00000105695 | MAG | 0.165266628900020962 | 0.076405826338611799 | 0.165266628900020962 |
| ENSG00000184512 | ANKRD35 | 0.163297656984657540 | 0.100393926874815490 | 0.163297656984657540 |
| ENSG00000145147 | SLIT2 | 0.162788345276333480 | 0.065886682012506307 | 0.162788345276333480 |
| ENSG00000151150 | ANK3 | 0.155840291151485140 | 0.141501100873699759 | 0.155840291151485140 |
| ENSG00000120324 | PCDHB10 | 0.152092596630804710 | 0.091725176385198700 | 0.152092596630804710 |
| ENSG00000142273 | CBLC | 0.152074262905099040 | 0.127619392645274600 | 0.152074262905099040 |
| ENSG00000137843 | PAK6 | 0.151421805478671 | 0.061013076665510900 | 0.151421805478671 |
| ENSG00000167258 | CDK12 | 0.150405362849483740 | 0.126635947207407858 | 0.150405362849483740 |
| ENSG00000172116 | CD8B | -0.089936580174755200 | 0.114972556137894730 | 0.089936580174755200 |

FIG. 2C

| gene_id | Gene Symbol | Mean coefficient | S.D coefficient | Absolute value of mean |
|---|---|---|---|---|
| ENSG00000144230 | SLC4A10 | -0.752935971174065898 | 0.086966184914098055 | 0.752935971174065898 |
| ENSG00000132465 | JCHAIN | -0.684806399063326867 | 0.199877971264220558 | 0.684806399063326867 |
| ENSG00000173114 | LRRN3 | -0.642758633739701 | 0.076833339860095736 | 0.642758633739701 |
| ENSG00000091129 | NRCAM | -0.637919626025086 | 0.143625273836248 | 0.637919626025086 |
| ENSG00000062524 | LTK | -0.627284933714747 | 0.090132264353086 | 0.627284933714747 |
| ENSG00000174807 | CD248 | -0.573188575129828 | 0.143856408159321377 | 0.573188575129828 |
| ENSG00000117322 | CR2 | -0.564139719123146 | 0.072583394860477 | 0.564139719123146 |
| ENSG00000135318 | NT5E | -0.553508950725446 | 0.057784710760174144 | 0.553508950725446 |
| ENSG00000169855 | ROBO1 | -0.535734154799243 | 0.137556040913262 | 0.535734154799243 |
| ENSG00000154358 | OBSCN | -0.504523591510347 | 0.098311489023698 | 0.504523591510347 |
| ENSG00000081059 | TCF7 | -0.327324305107630 | 0.198970163812341 | 0.327324305107630 |
| ENSG00000099204 | ABLIM1 | -0.318469760372891 | 0.076548432016283 | 0.318469760372891 |
| ENSG00000154930 | TMSB4Y | -0.309584404886867 | 0.079783399723409 | 0.309584404886867 |
| 445347 | TARP | -0.309111951070202 | 0.132758914809345 | 0.309111951070202 |
| ENSG00000148143 | ZNF462 | -0.308763715686069 | 0.076392352251676 | 0.308763715686069 |
| ENSG00000163079 | DNALI1 | -0.306276481085363 | 0.095236815182465 | 0.306276481085363 |
| ENSG00000112394 | SLC16A10 | -0.283428281486213 | 0.051225289108546186 | 0.283428281486213 |
| ENSG00000134545 | KLRC1 | -0.292542491831951 | 0.086956032585377169 | 0.292542491831951 |
| ENSG00000110987 | BCL7A | -0.290176362462773 | 0.202828685319633 | 0.290176362462773 |
| ENSG00000143365 | RORC | -0.281397073978897 | 0.071365919782452 | 0.281397073978897 |
| ENSG00000156219 | ART3 | -0.280553339473869 | 0.196325891073135 | 0.280553339473869 |
| ENSG00000163701 | IL17RE | -0.278318631598896 | 0.059930476686073 | 0.278318631598896 |
| ENSG00000112486 | CCR6 | -0.278232109142333 | 0.046035281485372 | 0.278232109142333 |
| ENSG00000095585 | BLNK | -0.276949457040978 | 0.143276657807844 | 0.276949457040978 |
| ENSG00000145331 | TRMT10A | -0.272249628087794 | 0.062272454678577 | 0.272249628087794 |
| ENSG00000100630 | LGMN | -0.271805133998669 | 0.048871433054902 | 0.271805133998669 |
| ENSG00000148848 | ADAM12 | -0.267335950185832 | 0.074252139704828 | 0.267335950185832 |
| ENSG00000079689 | SCGN | -0.267035883520442 | 0.153907758628689 | 0.267035883520442 |
| ENSG00000170476 | MZB1 | -0.260444156327511 | 0.094246036079858 | 0.260444156327511 |
| ENSG00000110851 | ASIC1 | -0.250939173716715 | 0.068898520864134 | 0.250939173716715 |
| ENSG00000108477 | CEP41 | -0.242322186640577 | 0.116978132785970 | 0.242322186640577 |

FIG. 2D

| gene_id | Gene Symbol | Mean coefficient | S.D coefficient | Absolute value of mean |
|---|---|---|---|---|
| ENSG00000120057 | SFRP5 | -0.237478383235328012 | 0.094360127909370436 | 0.237478383235328012 |
| ENSG00000119772 | DNMT3A | -0.237173140176632384 | 0.078372354381178575 | 0.237173140176632284 |
| ENSG00000162714 | ZNF496 | -0.236592056899022476 | 0.056651856633844457 | 0.236592056899022476 |
| ENSG00000160191 | PDE9A | -0.230818933216517424 | 0.110494040712704191 | 0.230818933216517424 |
| ENSG00000161381 | PLXDC1 | -0.225587210543263711 | 0.094175863563653913 | 0.225587210543263711 |
| ENSG00000276903 | H2AC18 | -0.212671300919840522 | 0.079138748840802422 | 0.212671300919840522 |
| ENSG00000135919 | SERPINE2 | -0.209171915381443391 | 0.081528588492020471 | 0.209171915381443391 |
| ENSG00000101104 | PABPC1L | -0.204624205314413081 | 0.081350842613990171 | 0.204624205314413081 |
| ENSG00000128040 | SPINK2 | -0.191828917922233751 | 0.057283227507280286 | 0.191828917922233751 |
| ENSG00000213809 | KLRK1 | -0.190441192452818511 | 0.121367646972576951 | 0.190441192452818511 |
| ENSG00000152990 | ADGRA3 | -0.190022485257937441 | 0.084842460338050881 | 0.190022485257937441 |
| ENSG00000126467 | TSKS | -0.186745126684626621 | 0.108302990794750851 | 0.186745126684626621 |
| ENSG00000183691 | NOG | -0.185739318717966281 | 0.062379254980803471 | 0.185739318717966281 |
| ENSG00000181690 | PLAG1 | -0.182656138565360731 | 0.129653222286320691 | 0.182656138565360731 |
| ENSG00000239264 | TXNDC5 | -0.182292460783536411 | 0.058885971483017911 | 0.182292460783536411 |
| ENSG00000153563 | CD8A | -0.178552703859024161 | 0.134386611380471611 | 0.178552703859024161 |
| ENSG00000133863 | TEX15 | -0.174655269721701481 | 0.124901772191932311 | 0.174655269721701481 |
| ENSG00000254126 | CD8B2 | -0.170345124566606151 | 0.059750885875913021 | 0.170345124566606151 |
| ENSG00000100100 | PIK3IP1 | -0.169056105857285171 | 0.094574645376686771 | 0.169056105857285171 |
| ENSG00000164047 | CAMP | -0.161563980446887111 | 0.134765118781530511 | 0.161563980446887111 |
| ENSG00000089012 | SIRPG | -0.160321733518092261 | 0.118018378659620211 | 0.160321733518092261 |
| ENSG00000107447 | DNTT | -0.159267833345071741 | 0.104540692715127231 | 0.159267833345071741 |
| ENSG00000183668 | PSG9 | -0.157146037474415 | 0.156965858501692281 | 0.157146037474415 |
| ENSG00000177191 | B3GNT8 | -0.156355180007087181 | 0.059399894541248431 | 0.156355180007087181 |
| ENSG00000136802 | LRRC8A | -0.155187597098557781 | 0.098544753972942481 | 0.155187597098557781 |
| ENSG00000169918 | OTUD7A | -0.154038781837311101 | 0.113958893292050891 | 0.154038781837311101 |
| ENSG00000176083 | ZNF683 | -0.153887766736406551 | 0.156881841952504961 | 0.153887766736406551 |

FIG. 7

| | | | |
|---|---|---|---|
| TSHZ2 | GLDC | CD27 | SEC14L2 |
| NRCAM | AGMAT | RPL18A | SH3RF2 |
| LRRN3 | K06904 | RAB15 | ZNF154 |
| IGFBP3 | sagA | SGTB | nikA, cntA |
| CD248 | ZNF462 | drp35 | PHLDA3 |
| EDA | JCHAIN | MARCHF2 | fbaB |
| LTK | ADGRA3 | ADAMTSL5 | sspC |
| KIF21A | KLRK1 | glft2 | S100A10 |
| NUCB2 | ADAM12 | FBLN2 | CHN1 |
| SORCS3 | MEOX1 | IQCA1 | PXK |
| TCF7 | SFRP5 | UTY | VCAN |
| GREM2 | TCEAL2 | INPP4B | CCDC88A |
| CR2 | LEP | NR4A1 | WNT10A |
| RORC | FAM20A | NEFH | COMP |
| ISM1 | MXRA8 | RPS16 | CFH |
| NT5E | CISH | FSBP | TAFA1 |
| CCR7 | CD8B | TMEM156 | BATF |
| TBC1D8B | ZNF727 | FHIT | ZSCAN18 |
| SLC4A10 | KCNS1 | CACHD1 | PDE9A |
| NAP1L2 | DEPDC7 | spo0A | SCEL |
| ABLIM1 | ZNF577 | PCDHGA10 | EIF2AK1 |
| ELOVL4 | ARMC9 | VIM | FIGN |
| RGMB | PGAM, gpmA | MIPOL1 | DNTT |
| PCDHGB6 | RGL4 | CFAP97D2 | doxA |
| ROBO1 | PDGFRB | PIGR | COL4A3 |
| CACNA1I | TARP | PYHIN1 | LTBP4 |
| PDZK1IP1 | EMP1 | VWDE | |
| PCDHGA6 | FAM13A | PCDH17 | |
| ASIC1 | POF1B | CCDC124 | |
| ANXA1 | AHNAK | DNMT3A | |

BIOMARKERS FOR AGE

CROSS-REFERENCE TO RELATED APPLICATIONS

This application is a continuation of and claims priority to International Application No. PCT/US21/49187, filed on Sep. 6, 2021, which claims the benefit of priority of U.S. Provisional Application 63/075,072, filed on Sep. 4, 2020, which is incorporated herein by reference in its entirety.

STATEMENT AS TO FEDERALLY SPONSORED RESEARCH

None.

THE NAMES OF THE PARTIES TO A JOINT RESEARCH AGREEMENT

None.

SEQUENCE LISTING

None.

BACKGROUND

Recent research has proposed computational aging clocks based on various biomarkers including metabolites, blood cell count and other routine lab tests (Earls et al., 2019; Momoshina, Kochetov et al. 2018), DNA methylation (Fraga & Esteller, 2007; Horvath & Raj 2018; Bell et al. 2019), gene expression in tissue (Momoshina, Volosnikova et al. 2018) or blood (Harries et al., 2011; Lin et al., 2019), taxonomic composition of the gut microbiome (Galkin et al., 2020), among others. Aging clocks propose to use a signal derived from these biomarkers as a health-related metric for aging, termed biological age.

Microbiome refers to the collection of microorganisms—bacteria, fungi and viruses—that inhabit the body of multicellular organisms. The microbiome inhabits many different parts of the human body, including, for example, mouth, throat, gut, skin, eye, nose, bronchi, urethra, and vagina. Microbes commonly found in the human microbiome include, for example, *Escherichia, Haemophilus, Streptococcus, Neisseria, Bacteroides, Clostridium, Mycobacterium, Pseudomonas, Spirochaeta* and *Mycoplasma*.

Microbiome composition (taxonomy) and activity can be associated with wellness and health conditions. Knowledge of such associations can be useful for the determination and treatment of such conditions. Alterations in a subject's microbiome content and activity can impact wellness and health.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein:

FIGS. 1A, 1B, 1C, 1D, 1E, and 1F show biomarkers for age taken from a microbiome metatranscriptome, including biomarkers representing both taxonomic designation and KEGG Orthology (KO) designation. Coefficient is determined by elastic net regression.

FIGS. 2A-2D show biomarkers for age taken from a blood meta-transcriptome. Biomarkers are identified by both ENSG (Ensemble Gene ID) and gene symbol. Coefficient is determined by elastic net regression. Markers with a positive coefficient are positively associated with age, while markers with a negative coefficient are negatively associated with age.

FIG. 7 shows biomarkers for age. Degree of association of the gene with age are generally arranged from high to low, by column, with columns arranged left to right in highest to lowest association.

SUMMARY

Figure 3A:
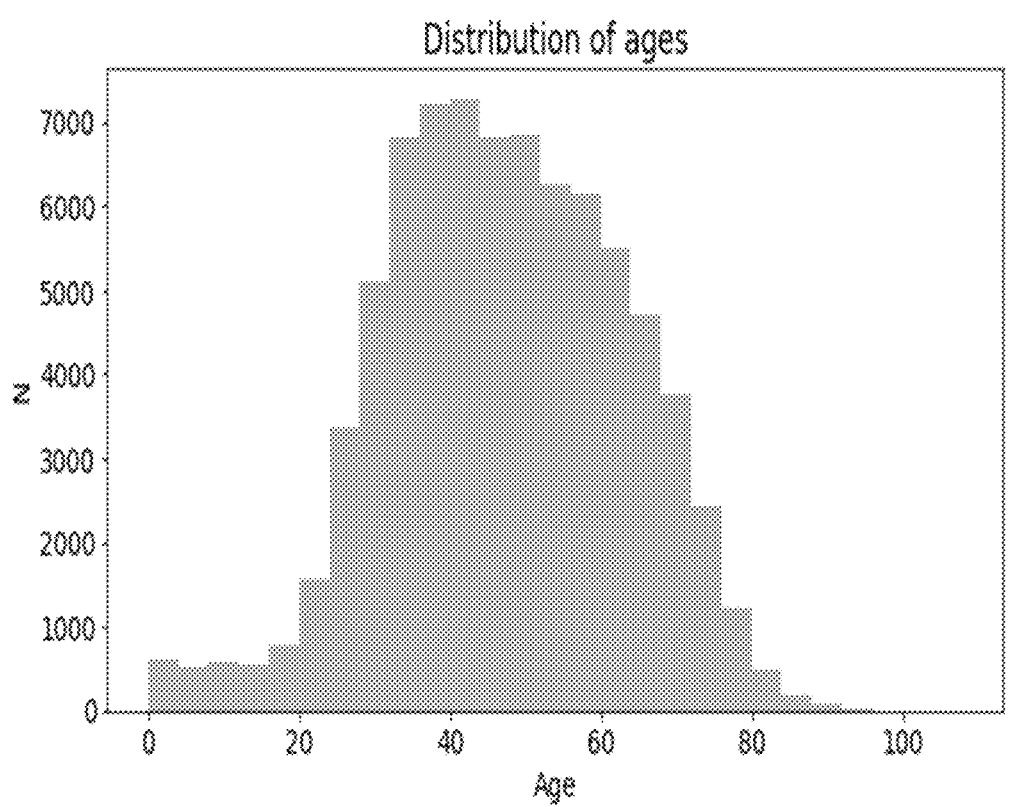
FIGS. 3A-3E show descriptive statistics for the microbiome discovery cohort (a) age distribution (b) richness and shannon diversity of active microbial richness by decade (c) richness and Pielou's evenness index for active functions (d-e) mean CLR transformed expression levels of species/KOs by age for most variable species/KOs.
Figure 3B:
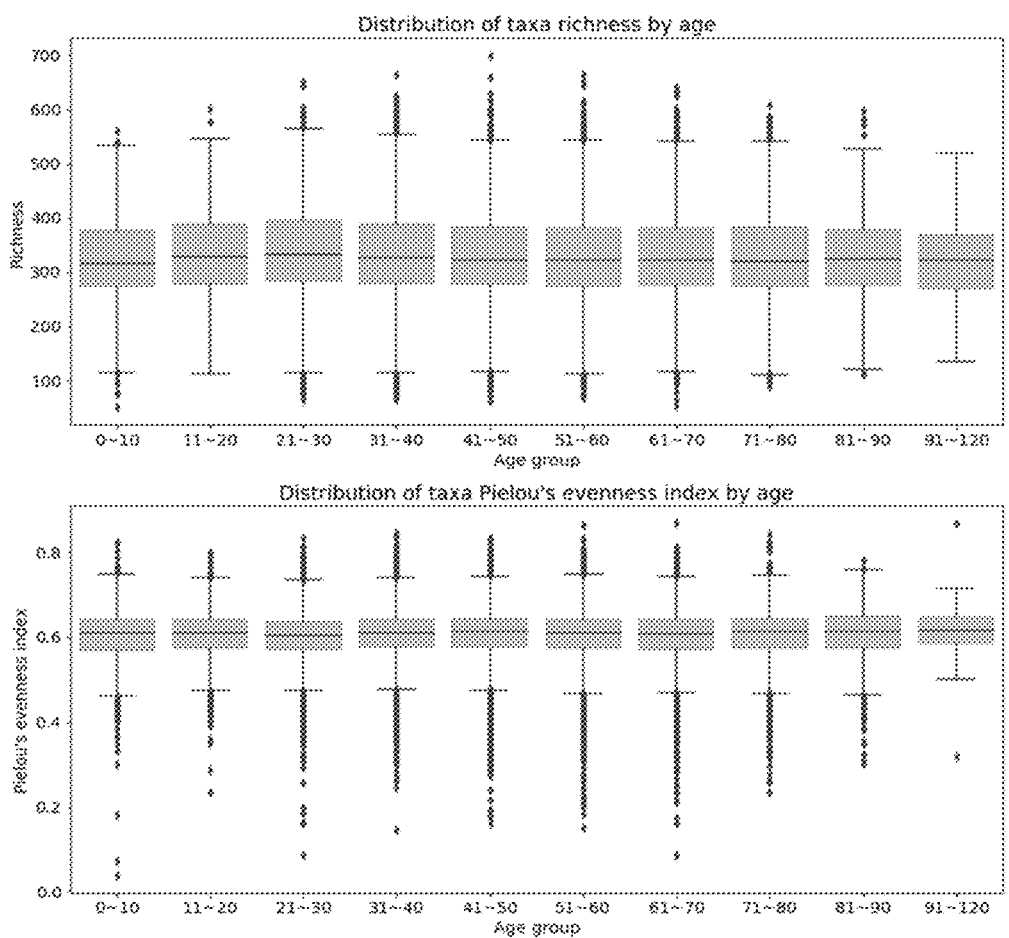
Figure 3C:
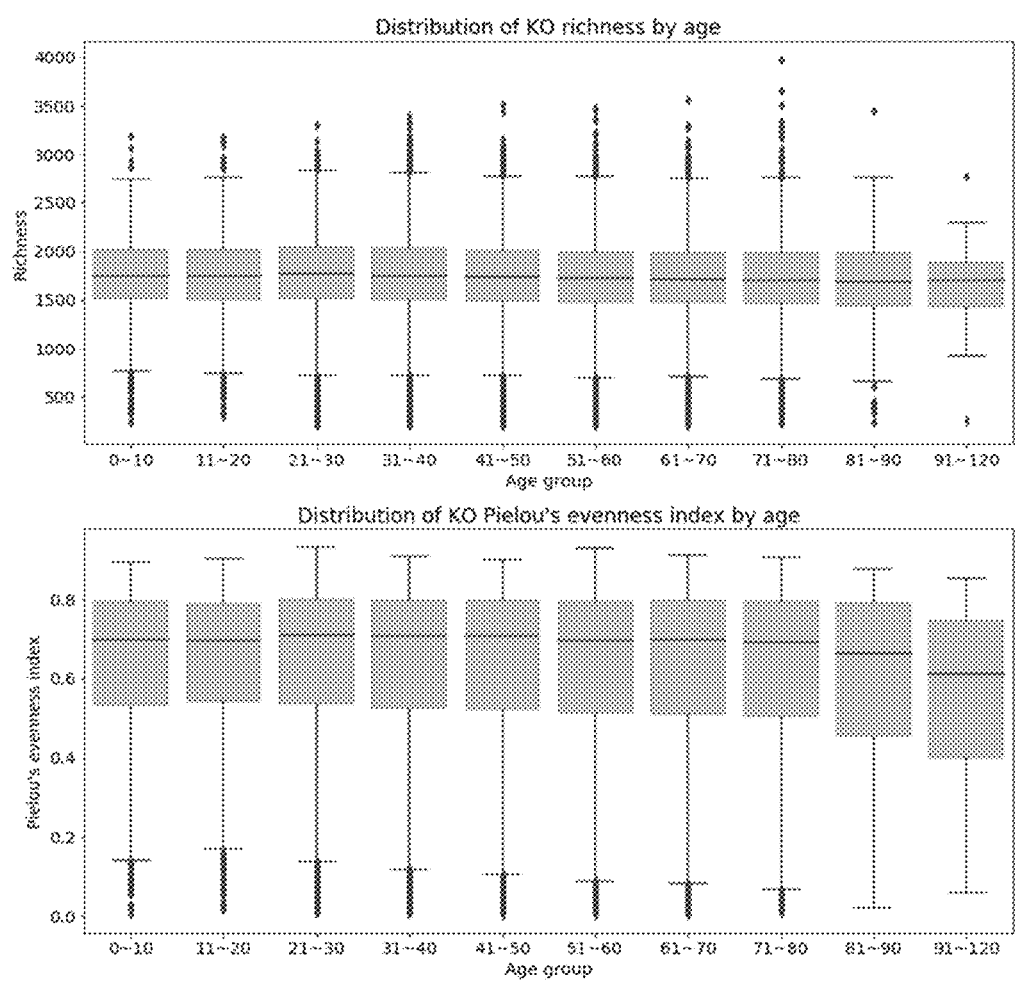
Figure 3D:
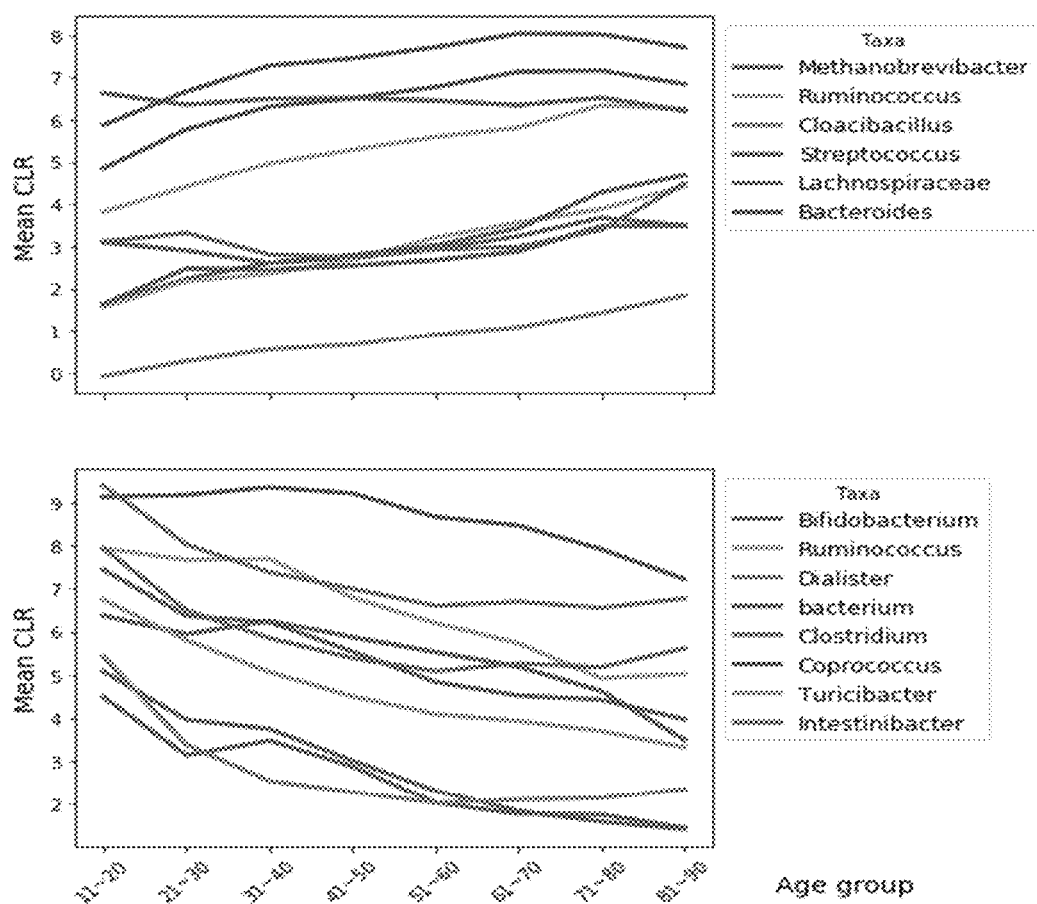
Figure 3E:
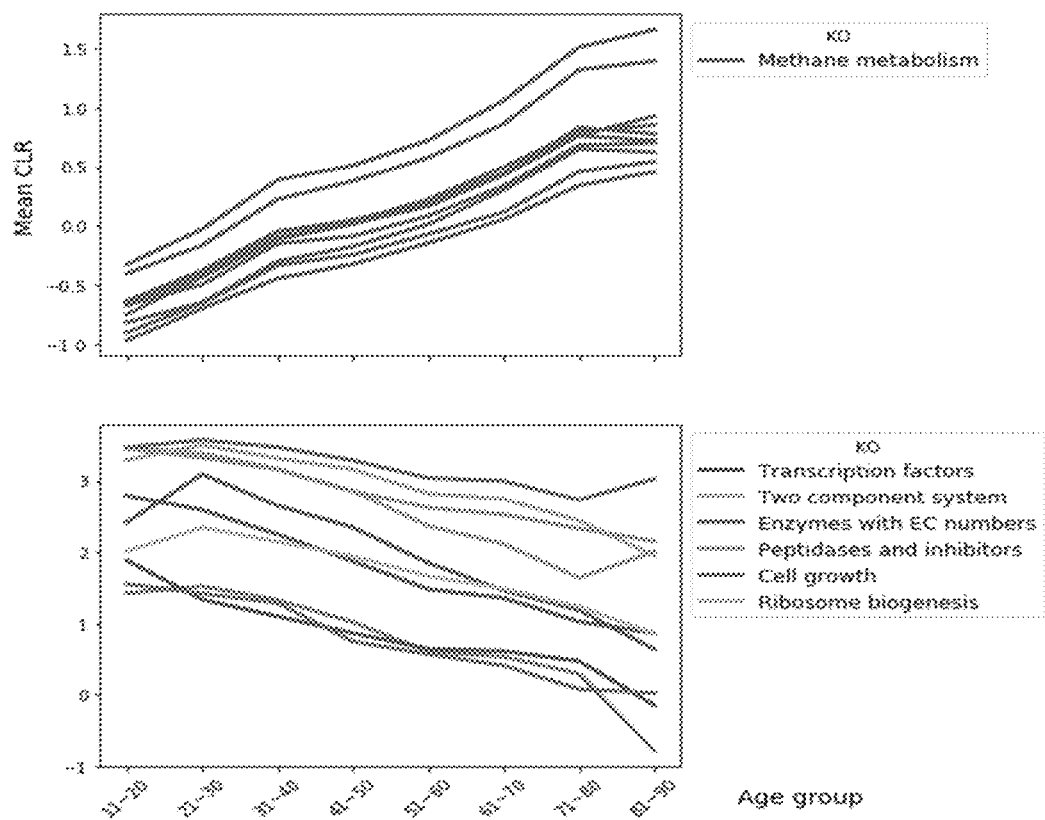

Measures of activity, based on metatranscriptomic data, of microbial taxa and gene or gene orthologs in a subject's microbiome and somatic cells, function as biomarkers for age. These biomarkers include activity of gene orthologs in either or both of the microbiome metagenome and the subject (e.g., a host) genome. It has also been found that aspects of a person's lifestyle or their health attributes are associated with a predicted age (biological age) that is greater or less than the subject's chronological age. Such aspects of lifestyle include being a heavy drinker or smoker, or being on a particular diet, such as vegetarian, vegan, keto, or paleo. Such health attributes include depression and diabetes. As such, the biomarkers disclosed herein are useful for predicting a subject's biological age. Such a prediction can then be used for a number of purposes, including, for example, providing wellness or therapeutic interventions to retard premature aging or to accelerate delayed aging.

DETAILED DESCRIPTION

I. Introduction

As used herein, the term "biomarker" refers to a biological molecule or biological trait, the presence, form or amount of which exhibits a statistically significant difference between two or more categories. Accordingly, biomarkers are useful, alone or in combination, for making inferences about a characteristic of a subject, and for classifying a subject into one of a plurality of groups.

As used herein, the term "biological age" refers to age as predicted by a model that predicts age using one or more biomarkers that are associated with chronological age. So, for example, if a person has a chronological age of 35, and the model predicts an age of 30, the person's biological age is 30. "Premature aging" refers to a condition in which a subject's biological age is greater than their chronological age. For example, a premature age can be at least any of 1 year, three years, five years of ten years greater than chronological age. "Delayed aging" refers to a condition in which a subject's biological age is less than their chronological age.

II. Sample Collection and Processing

A. Biological Samples

As used herein, the term "biological sample" refers to a sample that includes material of biological origin, such as cells, biological macromolecules (e.g., nucleic acids, proteins, carbohydrates or lipids) or their derivatives. Biological samples can comprise a host microbiome and/or subject (host) somatic cells. Somatic cells can be derived from any tissue of a subject, including blood (which includes leukocytes), skin, muscle, nerve, organs, etc.

The term "host" refers to an animal organism serving a vehicle for habitation of a microbiome. Animal hosts can include vertebrates or invertebrates, including fish, amphibians, reptiles, birds and mammals. Mammalian hosts can include primates and, in particular, humans. Mammalian hosts also can include farm animals and companion animals. A subject can be a host, and vice versa.

As used herein, the term "microbiome" includes a microbial community comprising one or a plurality of different microbial taxa inhabiting a host. As used herein, the term "gut microbiome" refers to a microbiome inhabiting a gut (e.g., stomach, intestine, colon) or throat, of a host. Samples comprising a microbiome can be obtained from, for example, gut, skin, mouth, nose, throat, and vagina. Microbial components of the microbiome can include bacteria, archaebacteria, viruses, fungi, and protists. Samples comprising a microbiome include, for example, feces, vaginal discharge, sputum, urine, saliva, secretions from the eye, and skin tissue.

Samples comprising transcriptomes from somatic cells include, for example, blood, cheek swab, tissue or organ biopsy, etc.

As used herein, the term "transcriptome" refers to the collection of RNA transcripts from a cell or cell type. In certain embodiments, a transcriptome is an mRNA transcriptome. The term "metatranscriptome" (MT) refers to a collection of transcriptomes taken from a collection of different cells or different microorganisms. So, for example, a microbiome transcriptome comprises a collection of transcriptomes from microbes in a microbiome. Somatic cell transcriptomes can be, for example, transcriptomes from cells in a blood sample, typically dominated by cells of lymphoid lineage.

Samples can be preserved for transport to a laboratory. The sample can be deposited into a container that comprises an aqueous liquid, e.g., a buffered solution. The aqueous liquid can further contain reagents to inhibit or slow degradation of one or more kinds of nucleic acid, such as DNA or RNA. As used herein, the term "nucleic acid preservative" refers to a compound or composition that inhibits degradation of nucleic acid. RNA preservatives include, without limitation, formalin, sulfate (e.g., ammonium sulfate), isothiocyanate (e.g., guanidinium isothiocyanate) and urea. Commercially available RNA preservatives include, for example, TRIzol (ThermoFisher), RNAlater (Ambion, Austin, TX, USA), Allprotect tissue reagent (Qiagen), PAXgene Blood RNA System (PreAnalytiX GmbH, Hombrechtikon), RNA/DNA Shield® (Zymo Research, Irvine, CA), and DNAstable (MilliporeSigma, Burlington, MA).

B. Sample Processing

Sample processing can proceed with cell lysis. Cell lysis can be performed by any method known in the art this can include, for example, bead beading, a method that involves rapidly shaking a container containing solid particles such that cells in the container are lysed.

Polynucleotides can be extracted directly from the sample, or cells in the sample can first be lysed to release their polynucleotides. In one method, lysing cells comprises bead beating (e.g., with zirconium beads). In another method, ultrasonic lysis is used. Such a step may not be necessary for isolating cell-free nucleic acids.

After cell lysis, samples are further processed by the extraction or isolation of biomolecules in the container, e.g., biomolecules released from lysed cells. Isolated biomolecules typically include nucleic acids such as DNA and/or RNA. Other biomolecules to be isolated can include polypeptides, such as proteins.

Isolation of biomolecules can be performed with a liquid-handling robot. After cell lysis, biological molecules, such as nucleic acids can be isolated or extracted from the sample Nucleic acids can be isolated from the sample by any means known in the art. Polynucleotides can be isolated from a sample by contacting the sample with a solid support comprising moieties that bind nucleic acids, e.g., a silica surface. For example, the solid support can be a column comprising silica or can comprise paramagnetic carboxylate coated beads or a silica membrane. After capturing nucleic acids in a sample, the beads can be immobilized with a magnet and impurities removed. In another method, nucleic acids can be isolated using cellulose, polyethylene glycol, or phenol/chloroform.

If the target polynucleotide is RNA, the sample can be exposed to an agent that degrades DNA, for example, a DNase. Commercially available DNase preparations include, for example, DNase I (Sigma-Aldrich), Turbo DNA-free (ThermoFisher) or RNase-Free DNase (Qiagen). Also, a Qiagen RNeasy kit can be used to purify RNA.

In another embodiment, a sample comprising DNA and RNA can be exposed to a low pH, for example, pH below pH 5, below pH 4 or below pH 3. At such pH, DNA is more subject to degradation than RNA.

DNA can be isolated with silica, cellulose, or other types of surfaces, e.g., Ampure SPRI beads. Kits for such procedures are commercially available from, e.g., Promega (Madison, WI) or Qiagen (Venlo, Netherlands).

Isolation of nucleic acids can further include elimination of non-informative RNA species from the sample. As used herein, the term "non-informative RNA" refers to a form of non-target or non-analyte species of RNA. Non-informative RNA species can include one or more of: human ribosomal RNA (rRNA), human transfer RNA (tRNA), microbial rRNA, and microbial tRNA. Non-informative RNA species can further comprise one or more of the most abundant mRNA species in a sample, for example, hemoglobin and myoglobin in a blood sample. Non-informative RNAs can be removed by contacting the sample with polynucleotide probes that hybridize with the non-informative species and that are attached to solid particles which can be removed from the sample. Examples of sequences that can be removed include microbial ribosomal RNA, including 16S rRNA, 5S rRNA, and 23S rRNA. Other examples of sequences that can be removed include host RNA. Examples include host rRNA, such as 18S rRNA, 5S rRNA, and 28S rRNA.

Isolated nucleic acids can be further processed to produce nucleic acid libraries. Production of nucleic acid libraries typically includes, in the case of RNA, converting RNA into DNA, e.g., by reverse transcription. Adaptors adapted for the DNA sequencing instrument to be used are typically attached to the DNA molecules.

According to one method, RNA molecules are reverse transcribed into cDNA using a reverse transcriptase. In certain embodiments, primers comprising a degenerate hexamer at their 3' end hybridize to RNA molecules. The reverse transcriptase extends the primer and can leave a terminal poly-G overhang. In certain embodiments, the primer can also comprise adapter sequences. A template molecule comprising a Poly-C overhang and, optionally, adapter sequences, can be hybridized to the poly-G overhang and used to guide extension to produce an adapter tagged cDNA molecule comprising a cDNA insert flanked by adapter sequences.

If the target polynucleotide is DNA, then DNA can be isolated with silica, cellulose, or other types of surfaces, e.g., Ampure SPRI beads. Kits for such procedures are commercially available from, e.g., Promega (Madison, WI) or Qiagen (Venlo, Netherlands).

Methods of enriching nucleic acid samples include the use of oligonucleotide probes. Such probes can be used for either positive selection or negative selection. Such methods often reduce the amount of non-target nucleotides.

Adapter tagged cDNA molecules can be amplified using well-known techniques such as PCR, to produce a library.

In certain embodiments the nucleic acids to be sequenced are comprised in the transcriptome. As used herein, the term "metatranscriptome" refers to the set of RNA molecules in a population of cells. This can include all RNAs, but sometimes refers to only mRNA. In the present context it generally refers to RNA molecules produced by either human or microbial cells. In certain embodiments, the nucleic acids to be sequenced can be free or essentially free of host nucleic acids ("host-free nucleic acids").

C. Nucleic Acid Sequencing

The isolated nucleic acids are generally sequenced for subsequent analysis. The methods described herein generally employ high throughput sequencing methods. As used herein, the term "high throughput sequencing" refers to the simultaneous or near simultaneous sequencing of thousands of nucleic acid molecules. High throughput sequencing is sometimes referred to as "next generation sequencing" or "massively parallel sequencing." Platforms for high throughput sequencing include, without limitation, massively parallel signature sequencing (MPSS), Polony sequencing, 454 pyrosequencing, Illumina (Solexa) sequencing, SOLiD sequencing, Ion Torrent semiconductor sequencing, DNA nanoball sequencing (Complete Genomics), Heliscope single molecule sequencing, single molecule real time (SMRT) sequencing (PacBio), and nanopore DNA sequencing (e.g., Oxford Nanopore). Nucleotide sequences of nucleic acids produced by sequencing are referred to herein as "sequence information" or "sequence data".

Also provided herein are methods of analyzing RNA transcripts in a heterogeneous microbial sample. The RNA transcripts can be part of a transcriptome for a cell or cells in the heterogeneous microbial sample. Information regarding the transcriptomes of a plurality of cells from different species may be obtained. The methods generally include isolating and sequencing the RNA found in a sample as described above.

Also provided herein are methods of analyzing RNA transcripts from a sample from a subject comprising somatic cells. The methods generally include isolating and sequencing the RNA found in a sample as described above.

III. Bioinformatics

Data used in developing a model to make the inferences described herein typically comprise large data sets including thousands, tens of thousands, hundreds of thousands or millions of individual measurements taken from or about a subject, typically at the systems biology level. The data can be derived from one or more (typically a plurality) different biological system components. These biological system components, also referred to herein as "feature groups", include, without limitation, the genome (genomic), the epigenome (epigenomic), the transcriptome (transcriptomic), the proteome (proteomic), the metabolome (metabolomic), the organismal cellular lipid components (lipidome), organismal sugar components of complex carbohydrates (glycomic), the proteome and/or genome of the immune system (immunomics) component of a system, organism phenotype (phenome, phenomic, phenotypic) and environmental exposure (exposome). (These are generally referred to herein as "-omic" data or information.)

The sequences obtained from these methods can be preprocessed prior to analysis. If the methods include sequencing a transcriptome, the transcriptome can be preprocessed prior to analysis. In one method, sequence reads for which there is paired end sequence data are selected. Alternatively, or in addition, in the case of analyzing the metatranscriptome of a microbiome, sequence reads that align to a reference genome of the host are removed from the collection. This produces a set of host-free transcriptome sequences. Alternatively, or in addition, sequence reads that encode non-target nucleotides can be removed prior to analysis. As described above, non-target nucleotides include those that are over-represented in a sample or non-informative of taxonomic information. Removing sequence reads that encode such non-target nucleotides can improve performance of the systems, methods, and databases described herein by limiting the sequence signature database to open reading frames (a part of a reading frame that has the ability to be translated) can the size of the database, the amount of memory required to run the sequence signature generation analysis, the number of CPU cycles required to run the sequence signature generation analysis, the amount of storage required to store the database, the amount of time needed to compare sample sequences to the database, the number of alignments that must be performed to identify sequence signatures in a sample, the amount of memory required to run the sequence signature sample analysis, the number of CPU cycles required to run the sequence signature sample analysis, etc.

A. Taxonomic Data

Subject data can include taxonomic data about the taxonomic classification and amounts of microbes in a microbiome of the subject. Such data is typically derived from nucleic acid sequence data obtained from the subject's microbiome. 16S RNA sequences are a standard source of information for assigning taxonomic classifications. Non-rRNA transcriptome data as an alternative source of information for taxonomic classification. Such methods are described in international patent publication WO 2018/

160899 ("Systems And Methods For Metagenomic Analysis"). Many metagenomic classifiers, aligners and profilers are publicly available. See, for example, Florian P Breitwieser et al., "A review of methods and databases for metagenomic classification and assembly," Briefings in Bioinformatics, Volume 20, Issue 4, July 2019, Pages 1125-1136, doi.org/10.1093/bib/bbx120, Published: Sep. 23, 2017. These include, without limitation, Centrifuge, GOTTCHA, kraken, kraken2, CLARK, Kaiju, MetaPhlAn, MetaPhlAn2, MEGAN, LMAT, MetaFlow, mOTUs, and mOTUs2.

Another method of analysis includes analysis of composition of microbiomes ("ANCOM"). This method is described in, for example, Mandal S, et al., "Analysis of composition of microbiomes: a novel method for studying microbial composition", Microb Ecol Health Dis. 2015 May 29; 26:27663. doi: 10.3402/mehd.v26.27663. eCollection 2015.

Taxonomic analysis can involve searching a sequence catalog of microbiome sequences for matches with sequences in the dataset, e.g., meta-transcriptomic sequences. Matches are assigned to the proper taxonomic category. Numbers of matches with a taxonomic category can indicate quantities of microbes of that taxonomic category in the sample.

The classifications can be at one or a plurality of different taxonomic levels, typically down to the species or strain level. Sequencing reads that map to sequences in the sub-catalog can then be labeled with tags indicating the taxonomic category at each level. The taxonomic label is assigned. Such systems can include classical or modern taxonomic classification systems.

As used herein, the term "taxon" (plural "taxa") is a group of one or more populations of an organism or organisms seen by taxonomists to form a unit. A taxon is usually known by a particular name and given a particular ranking. For example, species are often designated using binomial nomenclature comprising a combination of a generic name for the genus and a specific name for the species. Likewise, subspecies are often designated using trinomial nomenclature comprising a generic name, a specific name, and a subspecific name. The taxonomic name for an organism at the taxonomic rank of genus is the generic name, the taxonomic name for an organism at the taxonomic rank of species is the specific name, and the taxonomic name for an organism at the taxonomic rank of subspecies is the subspecific name, when appropriate.

As used herein, the term "taxonomic level" refers to a level in a taxonomic hierarchy of organisms such as, strain, species, genus, family, order, class, phylum, and kingdom. In some embodiments, each taxonomic level includes a plurality of "taxonomic categories", that is, the different categories belonging to particular taxonomic level. Some taxonomic levels only include a single member.

As used herein, the term "species" is intended to encompass both morphological and molecular methods of categorization. Species can be defined by genetic similarity. In some embodiments, a cladistic species is an evolutionarily divergent lineage and is the smallest group of populations that can be distinguished by a unique set of morphological or genetic traits.

Genomes imported into the reference catalog are typically indexed with a genome number. Various taxonomy indices, such as the NCBI taxonomy, categorized each genome number into a taxonomic classification. Consequently, sequencing reads that match reference sequences can also be taxonomically classified based on the number. Accordingly, using a taxonomic tree implicit in the taxonomic designation taxonomic source of any sequencing read can be identified and classified.

Once classified, sequences in each category can be quantified or estimated to determine amounts of sequencing reads in each taxonomic category and the relative abundance of each taxonomic entity. The sequencing reads can be meta-transcriptomic in origin. Accordingly, amounts of reads in a taxon represent transcriptional activity of the taxon, rather than pure numbers of organisms in the taxon in the sample.

B. Gene Expression Quantitation

The methods, systems and databases herein can be used to identify activity of a gene ortholog, a biochemical pathway or a functional activity from microbes present in the sample, or from somatic cells of a subject, e.g., analyze human gene expression. In some embodiments, the methods include aligning sequencing reads to a database comprising open reading frame information that is associated with a particular biochemical activity or pathway. Bioinformatic software to extract such information from sequence data is known in the art. Some of such methods can include identifying taxonomic information for a sequence. Examples include the VIOMEGA algorithm (see WO 2018/160899 (Vuyisich et al.)) or GOTTCHA algorithm, which detects sequence signatures that identify nucleic acids as originating from organisms at various taxonomic levels. Nucleic Acids Res. May 26, 2015; 43 (10): e69. Other methods include MetaPhlAn, Bowtie2, mOTUs, Kraken, and BLAST. Some of such methods do not include identifying taxonomic information for the sequence, but instead may identify the biochemical activity, pathway, protein, functional RNA, product, or metabolite associated with a particular sequence read or sequence signature.

"Gene expression," "gene activity" or "activity of a gene" is generally a function of transcription, e.g., the quantity of RNA in a sample encoding the gene. This can be done at any taxonomic level. For example, gene activity could be a measure of activity of the gene in a single species, or it could be activity of the gene across organisms belonging to a common genus, class, order or phylum. Thus, the term "gene" can refer to a gene in a single species, e.g., a somatic cells of a subject, or orthologs of a gene across different species, e.g., in different species of a microbiome. As used herein, the term "gene ortholog" refers to a homologous version of a gene across different taxa having the same biological function. Typically, gene orthologs share a high degree of sequence identity. Such orthologs can be identified, for example, with the KEGG orthology. Kanehisa, M. and Goto, S.; KEGG: Kyoto Encyclopedia of Genes and Genomes. Nucleic Acids Res. 28, 27-30 (2000)). KO (KEGG Orthology) databases. The KO (KEGG Orthology) database is a database of molecular functions represented in terms of functional orthologs. The KO databases include, among other things, genomic information, chemical information and systems information such as biological pathway maps. A functional ortholog is manually defined in the context of KEGG molecular networks, namely, KEGG pathway maps, BRITE hierarchies and KEGG modules. In the KEGG orthology, orthologs are identified by number. So, for example, "K01808" refers to rpiB; ribose 5-phosphate isomerase B [EC:5.3.1.6]. Search at the world wide web site genome.jp/kegg/kegg2.html. In some embodiments, where a single species is present, the term "gene ortholog" may refer to a single gene.

The KEGG orthology includes a hierarchy of levels. Level 1 (the top level) includes categories such as metabolism, genetic information processing, environmental information processing, cellular processes and human diseases. Level 2, in the metabolism category, includes categories for classes of molecules, such as carbohydrate, energy, lipid, nucleotide, amino acid, etc. Level 3 includes biochemical pathways. Level 4 includes specific genes and gene orthologs. In some embodiments, measure of activity used in the models described herein are measures of items at Level 4 of the KEGG orthology.

Nucleic acid sequence information is processed using bioinformatics to extract higher order information. In particular, two types of information that are usefully extracted from sequence data include gene activity information and taxa activity information.

The activities of one or more taxa groups can be determined from the amount of nucleic acid, e.g., RNA, in a sample originating from particular taxonomic groups. Microbial taxa include taxonomic designation at any taxonomic level, e.g., species, genus, order, class, or phylum. Active microbial taxa are taxa that are not merely present but that are metabolically active, e.g., as measured by transcriptional levels of the microbial genome. Taxa groups of interest include, without limitation, *Prevotella* (genus)/ *Bacteroides* (genus) ratio, *Eubacterium rectale* (species), *Eubacterium eligens* (species), *Faecalibacterium prausnitzii* (species), *Akkermansia muciniphila* (species), metabolic-related probiotic species (functional group), *Roseburia* (genus), *Bifidobacterium* (genus), *Lactobacillus* (genus), *Clostridium butyricum* (species), *Allobaculum* (genus), Firmicutes (phylum)/Bacteroidetes (phylum) ratio, Lachnospiraceae (family), Enterobacteriaceae (family), *Ralstonia pickettii* (species), *Bilophila wadsworthia* (species).

"Functional activities" are biological activity categories including biological or health functions or conditions at the cellular, organ or organismal level. Functional activities are assigned functional activity scores based on such data. Functional activity scores represent quantitative measures of functional activity. A functional category can involve any function related to health or wellness. Functional categories can embrace health parameters, health indicators, biological conditions and health risks. The activity of the function is assessed by analyzing -omic, e.g., transcriptomic data, which is collected from active, living organisms, e.g., expressing RNA from their genomes.

Functional activity includes integrative functional activities and non-integrative functional activities. Non-integrative functional activities are based on a single type of data or function, such as microbiome pathway activity data, taxa group activity data and host transcriptomic data. Integrative functional activities are based on an be based on a plurality of different kinds of data or functions. For example, such functional activities can combine pathway activity data in taxa activity data.

In certain embodiments, functional activities include the activities of one or more pathways. As used herein, the term "pathways" refers to biological pathways, which are sequences of proven molecular events (such as enzymatic reactions or signal transduction or transport of substances or morphological structure changes) that lead to specific functional outcomes (such as secretion of substances, sporulation, biofilm formation, motility). Many biological pathways are known in the art, and examples can be found on the web at wikipathways.org/index.php/WikiPathways, pathwaycommons.org, and proteinlounge.com/Pathway/Pathways.aspx. Manual expert curation of scientific literature also can be used to reconstruct or create custom biological pathways. Biological pathways can include a number of genes that encode peptides or proteins, which play specific signaling, metabolic, structural or other biochemical roles in order to carry out various molecular pathways.

As used herein, the terms "biochemical activity" and "biochemical pathway activity" refer to activity of a biochemical pathway. Pathways of interest include, without limitation, butyrate production pathways, LPS biosynthesis pathways, methane gas production pathways, sulfide gas production pathways, flagellar assembly pathways, ammonia production pathways, putrescine production pathways, oxalate metabolism pathways, uric acid production pathways, salt stress pathways, biofilm chemotaxis in virulence pathways, TMA production pathways, primary bile acid pathways, secondary bile acid pathways, acetate pathways, propionate pathways, branched chain amino acid pathways, long chain fatty acid metabolism pathways, long chain carbohydrate metabolic pathways, cadaverine production pathways, tryptophan pathways, starch metabolism pathways, fucose metabolism pathways.

IV. Data Collection

In order to build models to make inferences about biological age and trends in biological age, a dataset must be assembled that includes data from a plurality of subjects. Subjects typically will include both those diagnosed as having biological age and those diagnosed as not having biological age. The number of subjects in each category should be sufficient to provide statistically meaningful results. For example, such a cohort can comprise at least any of 50, 100, 500, or 1000 subjects diagnosed with the disease and at least any of 50, 100, 500, or 1000 subjects diagnosed without the disease.

V. Data Analysis

As used herein, the terms "analyze" and "performing a statistical analysis" refer to performing any algorithm that transforms inputs into outputs. Forms of statistical analyses include, without limitation, statistical analyses, machine learning analyses and neural net analyses. The term "data" may include data received from various data sources, metadata associated with the data, and/or a combination of both data and metadata.

A. Data Sets

In building or executing a model to predict the biological age of an individual subject, databases are provided that include information about one or a plurality of subjects. Raw data can include sequence data or information derived therefrom.

Models, or classification models, are algorithms that make inferences based on feature data measured from a test. Methods of generating models to predict biological age can involve providing a training dataset on which a machine learning algorithm can be trained to develop one or more models to predict biological age. The training dataset will include a plurality of training examples or instances, typically for each of a plurality of subjects and typically in the form of a vector. Each training example will include a plurality of features and, for each feature, data, e.g., in the form of numbers or descriptors. Where learning is to be supervised, the data will include a measure for a categorical or continuous variable, in this case, the subject's chronological age. For example, the continuous variable to be inferred may be "biological age" which can be given as any annualized age. Typically, for machine learning, the training examples will have at least 10, at least 100, at least 500 or at least 1000 different features. The features selected are those on which prediction will be based. In the present case features can include genes or taxa or gene activity and/or taxa activity. The collection of features included in a dataset can be referred to as a "feature set".

Accordingly, the collection of sequence data or gene activity and/or taxa activity data from an individual subject represent data for a particular instance. Each gene or taxon measured or determined represents a feature. A value, which can be a number or qualifier, is provided for an instance at a particular feature. The collection of data across a plurality of instances or examples, e.g. subjects, represents a dataset. Accordingly, each dataset can be represented as a vector of values for combinations of instances and features.

A measurement of a variable, such as a phenotypic trait (e.g., age), quantity of microbes in a taxon, gene expression levels, biochemical pathway activity or a functional activity, can be any combination of numbers and words. A measure can be any scale, including nominal (e.g., name or category), ordinal (e.g., hierarchical order of categories), interval (distance between members of an order), ratio (interval compared to a meaningful "0"), or a cardinal number measurement that counts the number of things in a set. Measurements of a variable on a nominal scale indicate a name or category (e.g., a class label), such a "cancer" or "non-cancer", "old" or "young", "form 1" or "form 2", "subject 1 . . . subject n," etc. Measurements of a variable on an ordinal scale produce a ranking, such as "first", "second", "third"; or order from most to least. Measurements on a ratio scale include, for example, any measure on a pre-defined scale, such as number of molecules, weight, activity level, signal strength, concentration, age (e.g, "20 years old" or "42 years 9 months old" or "65 years 2 months old"), etc., as well as statistical measurements such as frequency, mean, median, standard deviation, or quantile. Measurements on a ratio scale can be relative amounts or normalized measures. Quantitative measures can be given as a discrete or continuous range. Examples of quantitative measures include a number, a degree, a level, a range or bucket. A number can be a number on a scale, for example 1-10. Alternatively, the score can embrace a range. For example, ranges can be high, medium and low; severe, moderate and mild; or actionable and non-actionable. Buckets Can comprise discrete numerals, such as 1-3, 4-6 and 7-10.

A. Model Generation and Inferring Biological Age

Models can be created by statistical methods. Statistical analysis can include any useful methodology including, without limitation, correlational, Pearson correlation, Spearman correlation, chi-square, comparison of means (e.g., paired T-test, independent T-test, ANOVA) regression analysis (e.g., simple regression, multiple regression, linear regression, non-linear regression, logistic regression, polynomial regression, stepwise regression, ridge regression, lasso regression, elastic net regression) or non-parametric analysis (e.g., Wilcoxon rank-sum test, Wilcoxon sign-rank test, sign test). Statistical analysis can be performed by hand or by computer. Computer methods include, for example, machine learning algorithms.

Machine learning involves training machine learning algorithms on training data sets comprising data from a plurality of test subjects. Machine learning algorithms are trained on the training dataset to generate models that predict the biological age of an individual based on sequence data or information derived therefrom. Predicted biological age can be translated into recommendations to the subject about therapeutic interventions to be taken.

The machine learning algorithm can be any suitable supervised machine learning algorithm, parametric or non-parametric. Machine learning algorithms include, without limitation, artificial neural networks (e.g., back propagation networks), decision trees (e.g., recursive partitioning processes, CART), random forests, discriminant analyses (e.g., Bayesian classifier or Fischer analysis), linear classifiers (e.g., multiple linear regression (MLR), partial least squares (PLS) regression, principal components regression (PCR)), elastic net regression, mixed or random-effects models, non-parametric classifiers (e.g., k-nearest neighbors), support vector machines, and ensemble methods (e.g., bagging, boosting).

Methods for generating models to predict biological age can comprise the following operations. A dataset as described above is provided. The dataset includes, for each of a plurality of subjects, raw or processed data. The data set is used as a training dataset to train a machine learning algorithm to produce one or more models that predict biological age of a subject based on biomarkers identified from the data.

Biomarkers can be individual features used by the model in making an inference (e.g., prediction) of the variable in question. For example, of thousands of features used in the original training dataset, the model may use no more than any of 1, 5, 10, 50, 100 or 500 features in determining the inferred variable.

A. Validation

A model may be subsequently validated using a validation dataset. Validation datasets typically include data on the same features as the training dataset. The model is executed on the training dataset and the number of true positives, true negatives, false positives and false negatives is determined, as a measure of performance of the model.

The model can then be tested on a validation dataset to determine its usefulness. Typically, a learning algorithm will generate a plurality of models. In certain embodiments, models can be validated based on fidelity to standard clinical measures used to diagnose the condition under consideration. One or more of these can be selected based on its performance characteristics.

VI. Inferring Biological Age in a Subject

Inferring biological age in subject generally involves using a model to assign a predicted value, in this case, age, to a test subject. The classifier can classify the variable according to any classification scheme useful to the operator. The inferred result can be an age by year or a fraction of a year, or by a time range, such as two years, three years, five years, ten years, fifteen years or twenty years. The predicted age range can be skewed from the chronological age. For example, a range of ten years could be five years of either side (+5, −5) or seven years over and three years under (+7, −3). Alternatively, the inferred result can indicate a state such as "premature aging" or "retarded aging".

The model selected can either result from operator executed statistical analysis or machine learning. In any case, the model can be used to make inferences (e.g., predictions) about a test subject. Test data can be generated from one or more samples taken from the test subject. The test dataset can include all of the same features used in the training dataset, or a subset of these features. Such a subset function as biomarkers. The model is then applied to or executed on the test dataset. Inferring biological age is a form of executing a model. The inference is typically performed by computer, but can be performed by a person. The choice may depend on the complexity of the operation of correlating. This produces an inference, e.g., an assignment of a subject as having a variable characterized by a particular value (e.g., a particular age) or belonging to a class (e.g., prematurely aged).

The classifier or model may generate, from the subject data, a single number (e.g., age) which functions as the inference. Classifying a subject as having biological age can involve determining whether the number is above or below a threshold level associated with a normal number for the person's chronological age. A measure of central tendency, such as mean, median or mode, of numbers can be determined in a statistically significant number of normal and abnormal individuals. A cutoff above normal amounts can be selected as a diagnostic level of biological age. That number can be, for example, a certain degree of deviation from the measure of central tendency, such as variance or standard deviation. In one embodiment the measure of deviation is a Z score or number of standard deviations from the normal average.

The model used to make an inference of biological age can be chosen to have any desired level of sensitivity, specificity positive predictive value or negative predictive value. In one embodiment, sensitivity of the model is measured with reference chronological age, in particular, within a defined time range. So, for example, sensitivity may be measured by the number of subjects with a predicted age that is within three years over or under their chronological age.

Sensitivity refers to a value calculated according to the formula TP/(TP+FN), where TP is the number of true positive measurements (e.g., correctly inferring the presence of biological age in a subject) and FN is the number of false negative measurements (e.g., incorrectly inferring the absence of biological age in a subject). Sensitivity measures the percentage of subjects that actually have biological age who are inferred to have biological age by the test. In some embodiments, the diagnostic test can infer a presence or an absence of biological age with a sensitivity of greater than about any of: 70%, 75%, 80%, 85%, 86%, 87%, 88%, 89%, 90%, 91%, 92%, 93%, 94%, 95%, 96%, 97%, 98%, 99%, or 99.5%.

Specificity refers to a value calculated according to the formula TN/(TN+FP), where TN is the number of true negative measurements (e.g., correctly inferring an absence of biological age in a subject) and FP is the number of false positive measurements (e.g., incorrectly inferring the presence of biological age in a subject). Specificity measures the percentage of subjects that actually do not have biological age who are inferred to not have biological age by the test. In some embodiments, the diagnostic test can infer a presence or an absence of biological age with a specificity of greater than about any of: 70%, 75%, 80%, 85%, 86%, 87%, 88%, 89%, 90%, 91%, 92%1, 93%, 94%, 95%, 96%, 97%, 98%, 99%, or 99.5%.

Positive Predictive Value (PPV) refers to a value calculated according to the formula TP/(TP+FP). A PPV value is the proportion of subjects inferred to be positive (presence of biological age) that actually have biological age. In some embodiments, the model, e.g., diagnostic test, may infer a presence or an absence of biological age in a subject at a PPV of greater than about any of: 70%, 75%, 80%, 85%, 86%, 87%, 88%, 89%, 90%, 91%, 92%, 93%, 94%, 95%, 96%, 97%, 98%, 99%, or 99.5%.

Negative Predictive Value (NPV) refers to a value calculated according to the formula TN/(TN+FN). An NPV value is the proportion of subjects inferred to be negative (absence of biological age) that actually do not have biological age. In some embodiments, the model, e.g., diagnostic test, may infer a presence or an absence of biological age in a subject an NPV of greater than about any of: 70%, 75%, 80%, 85%, 86%, 87%, 88%, 89%, 90%, 91%%, 92%, 93%, 94%, 95%, 96%, 97%, 98%, 99%, or 99.5%.

Accuracy can be measured by the percentage of subjects who test positive or negative that are true positives or true negatives, respectively. Accuracy can be calculated using the following formula: Accuracy=(TP+TN)/(TP+TN+FP+FN).

Precision can be measured by the percentage of subjects who test positive that are true positives and not false positives. Precision can be calculated using the following formula: precision=TP/(TP+FP).

Classifications can be provided to a subject for example, in the form of recommendations. In one embodiment, the recommendations include a positive recommendation to administer a therapeutic intervention, e.g., a chemotherapy drug.

Individual features may be found to contribute more or less to making an inference. Such significant features can be determined, for example, by leaving them out of a training data set and determining the deterioration in predictive ability of the ultimate models. Also, to the extent statistical analysis generates a plurality of predictive models, comparison of such models can show certain features present in many models.

A. Metatranscriptome Features Associated with Age

FIG. 1, FIG. 2 and FIG. 7 identify biomarkers (microbial taxa, microbial gene orthologs and somatic cell (from blood) genes (identified as KEGG orthologs) associated with age.

Biomarkers used in the model can all be from a microbiome, all from somatic cells or a combination of both. Microbiome markers can all be taxonomic or all be gene orthologs, or a combination of both.

Biomarkers used in the methods disclosed herein can include one or a plurality of the biomarkers of FIG. 1, FIG. 2 and/or FIG. 7. Biomarkers used can include at least, exactly, or at most 1, 2, 3, 4, 5, 6, 7, 8, 9, 10, 20, 30, 40, 50, 60, 70, 80, 90, 100, 125, 150, 175, 200, 225 or all of the biomarkers of FIGS. 1 and 2. Biomarkers can include only one or more biomarkers of FIG. 1, FIG. 2 and/or FIG. 7, or can include other biomarkers as well, including non-molecular biomarkers, such as indices of lifestyle or health. Biomarkers can include or exclude microbial taxa, microbial gene orthologs or subject (e.g., host) gene orthologs, or combinations of these. Biomarkers can include those with coefficients having or excluding positive or negative values, that is, associated with premature (positive) aging or delayed (negative) aging. Biomarkers can include those having coefficients with an absolute value of at least any of 0.1, 0.2, 0.3, 0.4, 0.5, 0.6, 0.7 or 0.8.

Referring to FIG. 1, FIG. 2 and FIG. 7, biomarkers can be selected from those in each figure having the greatest absolute value coefficient. These greatest can include those among the top 40, top 20 or top 10 from each figure. They also can include those among the top 40, top 20 or top 10 from the figures combined. So, for example, the top 10 microbiome biomarkers in rank order of absolute value of coefficient are:

TABLE 1

| | |
|---|---|
| *Streptococcus gordonii* | 1.096848064 |
| *Propionibacterium acidifaciens* | 0.898507872 |
| *Streptococcus mutans* | 0.875641544 |
| *Turicibacter* sp. H121 | −0.815848332 |
| *Turicibacter sanguinis* | −0.751816485 |
| *Olsenella profusa* | 0.732465127 |

TABLE 1-continued

| | |
|---|---|
| Romboutsia timonensis | −0.724912035 |
| Haemophilus pittmaniae | −0.706798371 |
| Streptococcus vestibularis | 0.678402771 |
| Alloscardovia omnicolens | 0.675622463 |

VII. Methods of Wellness/Therapeutic Intervention

Provided herein are wellness/therapeutic interventions to alter rates of aging in a subject. This includes slowing the rate of aging. This includes retarding premature aging or promoting delayed aging in a subject.

As used herein, the terms "therapeutic intervention", "therapy" and "treatment" refer to an intervention that produces a therapeutic effect (e.g., treats) a pathological condition. A therapeutic effect is one that prevents, slows the progression of, delays the onset of symptoms of, improves the condition of (e.g., causes remission of), improves symptoms of, or cures a pathological condition, such as biological age.

As used herein, the term "effective" as modifying a therapeutic intervention or treatment (e.g., "therapeutic intervention effective to treat" or "an effective therapeutic intervention" or to amount of a pharmaceutical drug, supplement or food (e.g., "amount effective to treat" or "an effective amount"), refers to a therapeutic intervention or amount of such to produce a therapeutic effect. For example, for the given parameter, a therapeutic intervention effective to treat a condition will show an increase or decrease in the parameter of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

A therapeutic intervention can include, for example, administration of a treatment, administration of a pharmaceutical, or a biologic or nutraceutical substance with therapeutic intent. The response to a therapeutic intervention can be complete or partial. In some aspects, the severity of a condition is reduced by at least 10%, as compared, e.g., to the individual before administration or to a control individual not undergoing treatment. In some aspects the severity of the condition is reduced by at least 25%, 50%, 75%, 80%, or 90%, or in some cases, no longer detectable using standard diagnostic techniques.

A. Altering Expression Levels of Biomarkers

Execution of machine learning and other statistical methods can produce models that use features to infer age of a subject. In such models, levels of expression of particular features function as biomarkers of age. Changes in expression of these biomarkers over time represent a clock in which expression levels are associated with chronological age. A "normal" level of expression for a biomarker in a subject of a particular chronological age refers to an expression level in the subject that is within a normal range of expression for that chronological age. To the extent expression level of a biomarker is a function of chronological age in a model of aging, change across time of the expression level indicates a "normal" rate of aging. Accordingly, in certain embodiments, a biological age or a rate of aging can be altered by administration of a therapeutic intervention that re-sets one or more biomarkers to expression levels associated with a particular chronological age, or alters the rate of change in biomarker expression levels over time.

Thus, a rate of change can be slowed so that rather than changing at a normal level (e.g., one year per year), expression changes at a slower rate (e.g., one-half year per year).

One also may target a biomarker profile associated with a particular age and administer a therapeutic intervention to adjust expression levels to levels consistent with the target age. Such an age may be younger than a subject's chronological age, but also may be older, for example, in the case of a subject that may not be maturing physically at an acceptable rate.

Biological age or rates of aging in a subject can be altered by altering measured expression levels of such biomarkers towards levels of expression associated with younger or older chronological ages. In certain embodiments, this can mean normalizing expression levels of a biomarker, that is, altering aberrantly expressed biomarkers towards a value that is normal for a subject of that chronological age. Alternatively, it can mean altering the expression of the biomarker or biomarkers, even if they exist at normal levels, toward levels associated with younger or older chronological ages. For biomarkers whose expression is positively associated with advancing age, this can mean decreasing expression to retard aging or increasing expression to accelerate aging. For biomarkers the expression of which is negatively associated with advancing age, this can mean increasing expression to retard aging or decreasing expression to accelerate aging.

Treatments can include administration of therapeutic interventions to alter expression of one or more biomarkers toward a target expression level. Such interventions can include administration of therapeutic compositions that inhibit expression or activity of a gene, or promote expression or activity of the gene, depending on the direction one wishes to change aging. For example, to retard aging, one would decrease activity of a biomarker positively associated with age, or increase activity or a biomarker negatively correlated with age. The biomarker in question can be one or more of a taxonomic category of microbe, a gene ortholog in a microbe or a gene in the genome of a subject.

In certain embodiments, after inferring premature aging in a subject, the subject is provided with a therapeutic intervention to retard aging. Therapeutic interventions to retard aging include, for example, reduction or cessation of tobacco or alcohol consumption, or a vegetarian or vegan diet, and combinations of these.

Alternatively, activity of a biomarker can be increased by, for example, provision of a drug increases expression of a gene or increases growth of microorganisms. In another embodiment, expression of a gene can be increased using genetic engineering techniques, such as CRISPR, to modify the genome of a cell, for example, by increasing activity of a promoter operatively linked to the gene of interest.

B. Strategies for Therapeutic Intervention

Strategies for therapeutic intervention can be focused at a variety of different targets. Targets may be biomarkers, themselves, or the physiological result of activity of biomarkers, such as products of biochemical pathways, e.g., metabolites.

If the target is a metabolite:
- the metabolite can be sequestered and cleared from the tissue (stool, blood, saliva, CSF, etc.)
- the metabolite can be chemically modified into another molecule that does not lead to a disease state. This can be achieved using enzymes, reactive chemicals, inorganic catalysts, etc.
- the production of the metabolite can be inhibited, including 1) inhibiting any enzyme along the pathway that produces the metabolite 2) not introducing a substrate for the pathway, or 3) reducing the level of any intermediate metabolite along the pathway by sequestration or chemical modification.

the target of the metabolite can be modified to prevent the negative effects of the metabolite. For example, if the metabolite binds to a protein, peptide, nucleic acid, or another small molecule, inhibitors can be designed to prevent these interactions.

any downstream step that the metabolite affects may be targeted to prevent the negative effects. For example, if the metabolite is acting as a substrate for an enzyme, the enzyme inhibition would abolish the negative effects of the metabolite.

the production of the metabolite can be ceased if any nucleic acid component necessary for its production is removed, for example via CRISPR or anti-sense RNA.

the production of the metabolite may be inhibited by killing a microorganism or cells that produce it, via cytotoxins, antibiotics, bacteriophages, or immune therapy.

If the target is a peptide/protein:

the peptide/protein can be sequestered and cleared from the tissue (stool, blood, saliva, CSF, etc.)

the peptide/protein can be chemically modified and inactivated. This can be achieved using enzymes, reactive chemicals, inorganic catalysts, etc.

the production of the peptide/protein can be inhibited, including 1) inhibiting any biomolecule (for example, a transcription factor) necessary for the peptide/protein production or activation. This also includes the modification/removal of DNA/RNA via CRISPR or anti-sense RNA.

the target of the peptide/protein can be modified to prevent the negative effects of the peptide/protein If the peptide/protein binds to a protein, peptide, nucleic acid, or a small molecule, inhibitors can be designed to prevent these interactions.

any downstream step that the peptide/protein affects may be targeted to prevent the negative effects.

the production of the peptide/protein may be inhibited by killing a microorganism or cells that produce it, via cytotoxins, antibiotics, bacteriophages, or immune therapy If the target is a nucleic acid:

the nucleic acid can be sequestered and cleared from the tissue (stool, blood, saliva, CSF, etc.)

the nucleic acid can be chemically modified and inactivated. This can be achieved with enzymes, reactive chemicals, inorganic catalysts, etc.

the production of the nucleic acid can be inhibited, including 1) inhibiting any biomolecule (for example, a transcription factor) necessary for the nucleic acid production or activation. This also includes the modification/removal of DNA/RNA via CRISPR or anti-sense RNA.

the target of the nucleic acid can be modified to prevent the negative effects of the nucleic acid. If the nucleic acid binds to a protein, peptide, nucleic acid, or a small molecule, inhibitors can be designed to prevent these interactions.

any downstream step that the nucleic acid affects may be targeted to prevent the negative effects.

the production of the nucleic acid may be inhibited by killing a microorganism or cells that produce it, via cytotoxins, antibiotics, bacteriophages, or immune therapy If administration of a molecule (metabolite, peptide, protein, or nucleic acid) leads to a wellness/health state:

the molecule can be supplied orally. It may be protected from destruction by the digestive tract or premature absorption and targeted to the appropriate part of the GI tract.

the molecule can be supplied via IV injection, transdermal patch, or inhaler.

the molecule may be produced in vivo (intestines, blood, organ . . . ) using natural or provided mechanisms (such as enzymatic reactions) by providing substrates and necessary biological, chemical and physical components.

the molecule may be produced in vivo by enhancing transcription or translation of certain genes (activators or enhancers)

the molecule may be produced in vivo by inhibiting the transcription or translation of certain genes (e.g. repressors), via, for example anti-sense or miRNAs the molecule may be produced in vivo by removing certain genes, for example via CRISPR or similar mechanisms the molecule may be produced in vivo by installing specific biological entities, for example microorganisms, that produce it.

VIII. Drug Development

Biomarkers whose expression is positively associated with aging can be targets for drug development to inhibit expression or activity of the biomarker. This can include inhibiting activity of an over-expressed enzyme or inhibiting growth of microbes of a particular taxon. Accordingly, provided herein are methods comprising identifying a molecular biomarker whose expression is positively associated with chronological age; contacting the biomarker with a drug candidate; and determining whether the drug candidate inhibits activity or expression of the biomarker. If the biomarker is a microbial taxon, the method can involve contacting microbes of the taxon with a drug candidate and determining whether the drug candidate inhibits growth of the microbe. Methods for identifying drug candidates include contacting the biomarker molecule with the drug candidate and determining the effect on the activity of the biomarker, e.g., ability of the drug candidate to inhibit activity of the biomarker.

Drug candidates can include any type of molecule typically used for such purposes including, for example, biological molecules (e.g., recombinant proteins such as antibodies, peptides, nucleic acids such as siRNA), small organic molecules (non-biological organic molecules having a size up to about 5000 Da).

IX. Companion Diagnostic

Also provided herein are methods for using a companion diagnostic to infer response by a subject (e.g., will or will not respond positively or degree of response) to a therapeutic intervention to change rate of aging. A companion diagnostic is an in vitro diagnostic test or device that provides information relevant to the safe and effective use of a corresponding therapeutic intervention, a therapy or adjuvant therapy. Such methods can infer possible adverse reactions to a therapeutic intervention or can infer responsiveness to a therapeutic intervention. Such inferences may include schedule, dose, discontinuation, or combinations of therapeutic agents. In some embodiments, the therapeutic intervention is selected by measuring one or more biomarkers in the subject.

Companion diagnostics can be developed by generating a dataset that includes subjects that are responsive to and nonresponsive to a particular therapeutic intervention. The dataset will further include nucleic acid sequence information derived from one or more biological samples as described herein. The dataset can be subject to statistical analysis to identify features, e.g. biomarkers, useful in inferring responsiveness. In some embodiments, the data set is used as a training dataset to train a machine learning algorithm to generate a classification model to classify a subject as responsive or nonresponsive to the particular therapeutic intervention.

X. Computer Systems

Models provided herein can be executed by programmable digital computer.

Figure 8:
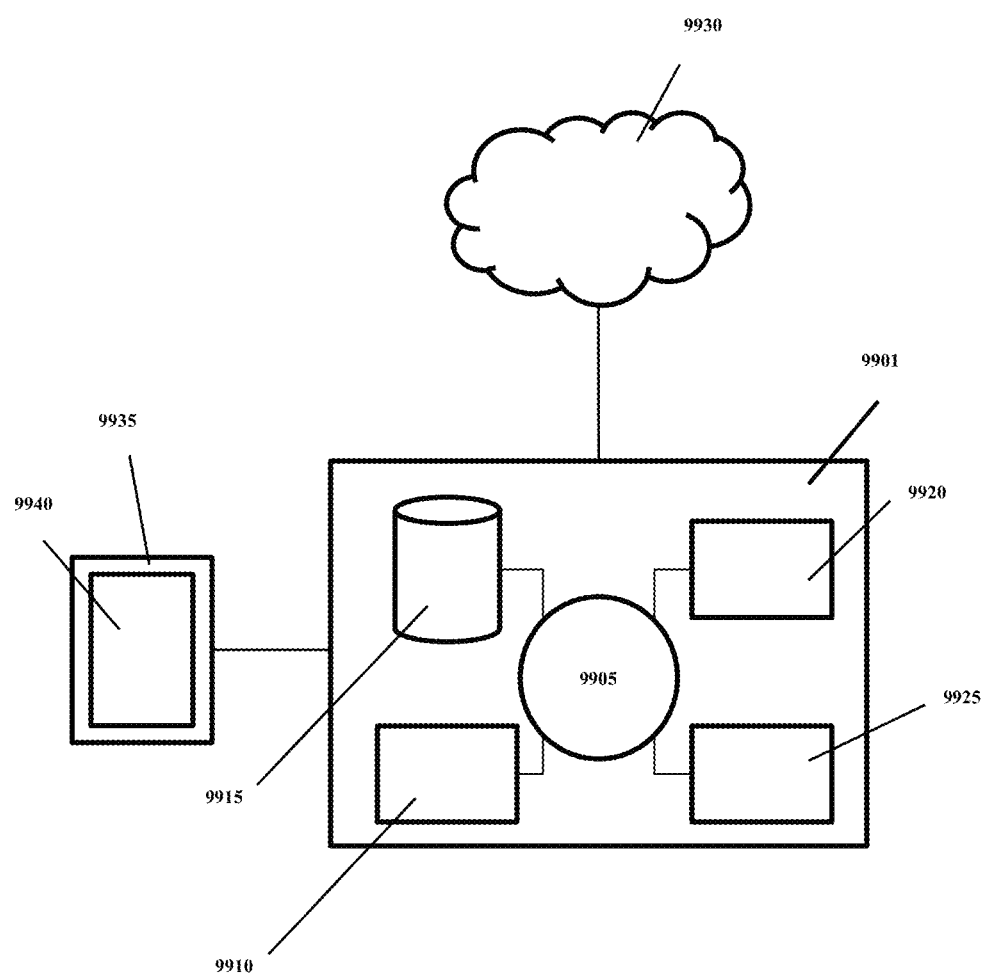
FIG. 8 shows an exemplary computer system.

FIG. 8 shows an exemplary computer system. The computer system 9901 includes a central processing unit (CPU, also "processor" and "computer processor" herein) 9905, which can be a single core or multi core processor, or a plurality of processors for parallel processing. The computer system 9901 also includes memory or memory location 9910 (e.g., random-access memory, read-only memory, flash memory), electronic storage unit 9915 (e.g., hard disk), communication interface 9920 (e.g., network adapter) for communicating with one or more other systems, and peripheral devices 9925, such as cache, other memory, data storage and/or electronic display adapters. The computer readable memory 9910, storage unit 9915, interface 9920 and peripheral devices 9925 are in communication with the CPU 9905 through a communication bus (solid lines), such as a motherboard. The storage unit 9915 can be a data storage unit (or data repository) for storing data. The computer system 9901 can be operatively coupled to a computer network ("network") 9930 with the aid of the communication interface 9920. The network 9930 can be the Internet, an internet and/or extranet, or an intranet and/or extranet that is in communication with the Internet. The network 9930 in some cases is a telecommunication and/or data network. The network 9930 can include one or more computer servers, which can enable distributed computing, such as cloud computing.

The CPU 9905 can execute a sequence of machine-readable instructions, which can be embodied in a program or software. The instructions may be stored in a memory location, such as the computer readable memory 9910. The instructions can be directed to the CPU 9905, which can subsequently program or otherwise configure the CPU 9905 to implement methods of the present disclosure.

The storage unit 9915 can store files, such as drivers, libraries and saved programs. The storage unit 9915 can store user data, e.g., user preferences and user programs. The computer system 9901 in some cases can include one or more additional data storage units that are external to the computer system 9901, such as located on a remote server that is in communication with the computer system 9901 through an intranet or the Internet.

The computer system 9901 can communicate with one or more remote computer systems through the network 9930.

Methods as described herein can be implemented by way of machine (e.g., computer processor) executable code stored on an electronic storage location of the computer system 9901, such as, for example, on the computer readable memory 9910 or electronic storage unit 9915. The machine executable or machine-readable code can be provided in the form of software. During use, the code can be executed by the processor 9905. In some cases, the code can be retrieved from the storage unit 9915 and stored on the memory 9910 for ready access by the processor 9905. In some situations, the electronic storage unit 9915 can be precluded, and machine-executable instructions are stored on memory 9910.

Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks.

The computer system 9901 can include or be in communication with an electronic display 9935 that comprises a user interface (UI) 9940 for providing, for example, input parameters for methods described herein. Examples of UIs include, without limitation, a graphical user interface (GUI) and web-based user interface.

Processes described here can be performed using one or more computer systems that can be networked together. Calculations can be performed in a cloud computing system in which data on the host computer is communicated through the communications network to a cloud computer that performs computations and that communicates, or outputs results to a user through a communications network. For example, nucleic acid sequencing can be performed on sequencing machines located at a user site. The resulting sequence data files can be transmitted to a cloud computing system where the sequence classification algorithm performs one or more operations of the methods described herein. At any step cloud computing system can transmit results of calculations back to the computer operated by the user.

Data can be transmitted electronically, e.g., over the Internet. Electronic communication can be, for example, over any communications network include, for example, a high-speed transmission network including, without limitation, Digital Subscriber Line (DSL), Cable Modem, Fiber, Wireless, Satellite and, Broadband over Powerlines (BPL). Information can be transmitted to a modem for transmission, e.g., wireless or wired transmission, to a computer such as a desktop computer. Alternatively, reports can be transmitted to a mobile device. Reports may be accessible through a subscription program in which a user accesses a website which displays the report. Reports can be transmitted to a user interface device accessible by the user. The user interface device could be, for example, a personal computer, a laptop, a smart phone or a wearable device, e.g., a watch, for example worn on the wrist.

XI. Communicating Results in Implementing Wellness/Therapeutic Interventions Inference models as described herein can be executed on subject data to produce predicted biological age and/or recommendations for wellness or therapeutic intervention. In one embodiment, after making an inference about biological age, the method can comprise developing a model for therapeutic intervention in the subject. The model can comprise, for example, those interventions described herein to alter the rate of aging. Such a model and be communicated to the subject, for example, transmitting the model and, optionally, the inference, to a user interface of a personal computing device of the subject.

Inferences on a subject's age and/or recommendations for wellness/therapeutic intervention can be provided to subjects through an Internet website. A website can be provided which can be accessed by a subject, e.g. a customer, through a password-protected portal. The website can include a clickable icon. Upon clicking the icon, the subject can receive personalized food recommendations. Such inferences and/or recommendations can be displayed on a webpage connected to the clickable icon. Subject can receive at an Internet connected server notification that inferences and/or recommendations for the subject are available.

After wellness/therapeutic interventions are implemented, the effect of these interventions on the subject's condition can be remeasured. Such remeasurements can be used to generate updated inferences and/or recommendations as described herein.

Exemplary Embodiments

Exemplary embodiments of the invention include, without limitation, the following:

1. A method for inferring biological age in a subject, comprising:
    a) providing one or more biological samples from a subject, wherein the one or more samples comprise nucleic acids from a microbiome of a subject and/or nucleic acids from somatic cells of the subject;
    b) sequencing the nucleic acids to produce sequence information;
    c) determining, from the sequence information, measures of activity of each of one or more microbial taxa and/or measures of activity of one or more genes or gene orthologs, wherein the one or more measures are included in a feature set;
    d) executing, by computer, a classification model that infers, from one or more features in the feature set, a biological age of the subject.
2. The method of embodiment 1, further comprising:
    d) outputting the inference to a user interface device or to computer-readable memory.
3. The method of embodiment 1, further comprising:
    d) delivering and/or administering to the subject a therapeutic intervention effective to alter the rate of biological aging.
4. The method of embodiment 1, wherein the subject is a human or non-human animal.
5. The method of embodiment 1, wherein the one or more biological samples comprise both a microbiome sample and a somatic cell sample.
6. The method of embodiment 5, wherein the microbiome sample comprises feces and the somatic cell sample comprises blood or a blood fraction.
7. The method of embodiment 5, wherein the microbiome sample is a gut microbiome sample and the somatic cell sample is a leukocyte sample.
8. The method of embodiment 1, wherein the nucleic acids comprise a microbiome metatranscriptome and/or a somatic cell metatranscriptome.
9. The method of embodiment 1, wherein microbial taxa are determined at the species level.
10. The method of embodiment 1, wherein the gene or gene ortholog is comprised in the KEGG Orthology.
11. The method of embodiment 1, wherein the measure of activity is a function of quantity of transcripts for a gene or gene ortholog.
12. The method of embodiment 1, wherein the classification model uses features selected from both microbial taxa activity and gene or gene ortholog activity.
13. The method of embodiment 1, wherein the classification model classifies biological age within a confidence interval (e.g., within any of one year, two years, three years, five years or ten years).
14. The method of embodiment 1, wherein the classification model uses one or more features selected from the features of FIG. 1, FIG. 2 and/or FIG. 7.
15. The method of embodiment 1, wherein the classification model uses at least, exactly or no more than any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, or 243, of the features selected from the features of FIG. 1, FIG. 2 or FIG. 7.
16. The method of embodiment 1, wherein the classification model uses one or more features selected from *Streptococcus gordonii, Propionibacterium acidifaciens, Streptococcus mutans, Turicibacter* sp. H121, *Turicibacter sanguinis, Olsenella profuse, Romboutsia timonensis, Haemophilus pittmaniae, Streptococcus vestibularis*, and *Alloscardovia omnicolens*.
17. The method of embodiment 1, wherein the classification model uses one or more features selected from TSHZ2, IGFBP3, NAP1L2, IL18, FAM13A, BCL2, GREM2, SORCS3, NR4A1, and ADAMTS1.
18. The method of embodiment 1, wherein the features of FIG. 1 include one or more microbial taxa features and/or one or more gene ortholog features.
19. The method of embodiment 1, wherein the features of FIG. 1 or FIG. 2 include one or more positively associated features and/or one or more negatively associated features.
20. The method of embodiment 1, wherein the classification model uses only features selected from the features of FIG. 1, FIG. 2 and/or FIG. 7.
21. The method of embodiment 1, wherein the model uses elastic net regression.
22. A method comprising:
    a) providing one or more biological samples from each of a plurality of subjects, wherein the one or more samples comprise nucleic acids from a microbiome and/or somatic nucleic acids from the subject, and wherein the plurality of subjects include a subjects of a plurality of different chronological ages;

b) sequencing nucleic acids in the biological samples to provide sequence information; and c) performing a statistical analysis on the sequence information to produce a model that infers a state of biological age in a subject based on sequence information.

23. The method of embodiment 22, wherein the statistical analysis comprises a model developed by machine learning.

24. A method comprising:

a) providing one or more biological samples from a subject, wherein the one or more samples comprise nucleic acids from a microbiome of a subject and/or nucleic acids from somatic cells of the subject;

b) sequencing nucleic acids in the biological sample to provide sequence information;

c) executing a model of embodiment 22, on the sequence information to infer a biological age in the subject based on the sequence information; and d) outputting the inference to a user interface device or to computer-readable memory.

25. A method comprising:

a) administering to a subject inferred to have biological age by a method of embodiment 1 that is higher that the subject's chronological age, a therapeutic intervention effective to slow the rate of aging.

26. The method of embodiment 25, wherein the therapeutic intervention comprises one or more of: (1) reduced consumption of tobacco; (2) reduced consumption of alcohol; and (3) a vegetarian or vegan diet.

27. A system comprising:

(a) a computer comprising: (i) a processor; and (II) a memory, coupled to the processor, the memory storing a module comprising:

(1) nucleic acid sequence information from one or more biological samples from a subject, wherein the one or more samples comprise nucleic acids from a microbiome of a subject and/or nucleic acids from somatic cells of the subject;

(2) a classification model which, based on values including the measurements, infers biological age of the subject, wherein the classification model is configured to have a sensitivity of at least 75%, at least 85% or at least 95%; and (3) computer executable instructions for implementing the classification model on the test data.

28. A method for developing a computer model for inferring, from feature data, a biological age of a subject, the method comprising:

a) training a machine learning algorithm on a training data set, wherein the training data set comprises, for each of a plurality of subjects, (1) chronological age of a subject; and (2) feature data comprising quantitative measures for each of a plurality of features selected from microbiome transcriptome and somatic cell transcriptome, and wherein the machine learning algorithm develops a model that infers an age-based class label for a subject based on the feature data.

29. A method that infers a biological age in a subject, the method comprising:

(a) providing a data set comprising, for the subject, feature data for each of a plurality of features selected from microbiome transcriptome and somatic cell transcriptome data; and (b) executing a computer model on the data set to infer the biological age in the subject.

30. A software product comprising a computer readable medium in tangible form comprising machine executable code, which, when executed by a computer processor, infers a state of biological age in a subject by:

(a) accessing a data set comprising, for a subject, feature data for each of a plurality of features selected from microbiome transcriptome and somatic cell transcriptome data; and (b) executing a computer model on the data set to infer a biological age of the subject.

31. A method for treating premature biological age in a subject comprising:

(a) receiving from a subject one or more biological samples from a subject, wherein the one or more samples comprise nucleic acids from a microbiome of a subject and/or nucleic acids from somatic cells;

(b) determining nucleic acid sequences of the nucleic acids;

(c) determining alignments of the nucleic acid sequence to reference nucleic acid sequences associated with biological age;

(d) generating a feature dataset for the subject based upon the alignments;

(e) generating an inference of premature aging in the subject upon processing the feature dataset with an inference model derived from a population of subjects;

(f) developing a therapeutic intervention for treatment of premature aging for the subject based on biomarkers in the feature set associated with premature aging; and (g) at an output device associated with the subject, providing the therapeutic intervention to the subject with premature aging.

32. A method comprising:

(a) measuring, in a sample from a subject comprising a microbiome transcriptome and/or a somatic cell transcriptome, activity of one or more biomarkers selected from FIG. 1, FIG. 2 and/or FIG. 7;

(b) inferring, from the measurements, premature aging of the subject; and (c) delivering to the subject a therapeutic intervention to treat the premature aging.

33. The method of embodiment 32, wherein measuring comprises:

optionally, amplifying microbial metatranscriptome sequences in the sample;

sequencing the microbial metatranscriptome from the sample to produce sequence reads;

searching reference sequences in a reference sequence catalog for matches with the sequence reads;

determining amounts of sequence reads matching references sequences in the catalog to produce a data set; and determining, from the data set, activity of each of the one or more biomarkers.

34. The method of embodiment 33, wherein determining activity comprises:

for biomarkers that are taxa categories, performing a taxonomic analysis with a metagenomic classifier to measure taxa activity;

for biomarkers that are genes or gene orthologs, performing a functional analysis by determining activity of genes having the same function across taxa based on sequences corresponding to microbial open reading frames (ORFs), and combining the activities to produce gene or gene ortholog activity.

35. The method of embodiment 32, wherein inferring comprises:

executing by computer a classification model that infers biological age based on the biomarkers.

36. The method of embodiment 32, wherein the therapeutic intervention is selected from a drug, a dietary supplement, a food ingredient, and a food.

37. The method of embodiment 32, wherein measuring comprises:
(i) selectively amplifying in the sample nucleic acids specific for the biomarkers; and
(ii) determining amounts of the amplified nucleic acids.

38. A method comprising:
a) providing biological samples from each of a first set of subjects and a second set of subjects having premature aging biological age and having been subject to a therapeutic intervention for premature aging, wherein the biological samples comprise nucleic acids from a microbiome, and/or host somatic cells, and wherein the first set of subjects responded positively to the therapeutic intervention and the second set of subjects did not respond positively to the therapeutic intervention;
b) sequencing nucleic acids in the biological samples to provide sequence information; and
c) performing a statistical analysis on the sequence information to produce a model that infers whether a subject will have a positive response or lack of positive response to the therapeutic intervention.

39. A method of treating a subject with premature aging comprising:
(a) inferring that the subject will respond positively to each of one or more therapeutic interventions by executing a model on nucleic acid information from a biological sample from the subject comprising a microbiome and/or somatic cells; and
(b) administering to the subject one or more of the therapeutic interventions.

40. A method comprising:
a) providing one or more biological samples from a subject, wherein the one or more samples comprise nucleic acids from a microbiome of a subject and/or nucleic acids from somatic cells of the subject;
b) sequencing the nucleic acids to produce sequence information;
c) determining, from the sequence information, measures of activity of each of one or more microbial taxa and/or measures of activity of one or more genes or gene orthologs, wherein the one or more measures are included as features in a feature set;
d) identifying from the feature set one or more biomarkers that are either over-expressed or under-expressed for a subject of the subject's chronological age; and
e) administering to the subject one or more therapeutic interventions that slows, decreases or normalizes expression of an over-expressed biomarker, or accelerates, increases or normalizes expression of an under-expressed biomarker.

41. A method comprising:
identifying, by a method as described herein, one or more biomarkers that are associated with chronological age in a subject; and
screening one or a plurality of drug candidates to determine whether the drug candidate increases or decreases expression or activity of the over-expressed or under-expressed feature.

42. The method of embodiment 41, wherein the biomarker is a biomarker of FIG. 1, FIG. 2 and/or FIG. 7.

43. A method comprising:
measuring, in a sample from a subject, activity of each of a plurality of biomarkers associated with age, wherein the biomarkers include one or more of microbial taxa, microbial gene orthologs or host gene orthologs;
identifying biomarkers that are over-expressed or under-expressed compared to normal; and
administering to the subject a therapeutic intervention that modifies activity of one or more biomarkers towards normal.

44. A method comprising:
a) administering to a subject a therapeutic intervention effective to alter activity of one or more biomarkers of FIG. 1, FIG. 2 and/or FIG. 7, wherein altering activity slows the rate of aging.

Examples

I. Methods

A. Study Cohorts

Microbiome. Each gut microbiome sample is from a unique customer, with samples with less than 50 taxa, less than 200 KOs, or less 5,000 total reads mapped to taxa removed. These samples were divided into a discovery cohort of 78,637 samples, and a validation cohort of 11,666 samples shown in Table 1. Stool samples were collected between April 2017 and June 2020. Baseline MAE is computed as MAE from the median age of the cohort. The discovery cohort was used to evaluate expected model generalization performance using cross validation, then a final model was trained on the full discovery cohort for evaluation. The final model was applied to the validation cohort (drawn from the same population but not used in training), cohorts matched to two validation datasets (CV and HC) analyzed in Galkin et al. (2020), and additional cohorts described in Cohort Comparisons below. The Galkin et al. matched cohorts are intended to allow comparison of this model to the one presented in that work, and were constructed by randomly choosing one Viome customer from our validation set with the same age as each person in the Galkin et al. datasets. One person in the matched CV cohort could not be paired with a unique sample in our data, so our cohort has 1164 samples rather than Galkin et al.'s 1165. For the HC cohort we additionally matched on sex, which was impossible in the larger CV cohort.

Human. The human blood transcriptome consists of samples obtained from 1494 unique participants and associated R&D studies. Gene expression levels were computed by aggregating transcripts per million estimates per gene using an approach based on Salmon (Patro et al., 2017), as described in Toma et al. (under review).

B. Data Preparation

All samples were processed using the metatranscriptomic method described in Hatch (2019), reads were mapped to genomes (Breitwieser et al., 2017) and to a catalog of microbial genes with KEGG ortholog (KO) annotations (Kanehisa & Goto, 2000), and quantified using the expectation-maximization algorithm (Dempster, et al. 1977). This yields two views of the relative activity of each gut microbiome sample, one taxonomic and one functional. The taxonomic view aggregates reads to the species level, while the functional view aggregates the same reads to KOs.

The microbiome data was transformed using the centered log ratio transformation (CLR) (Aitchison, 1986) after imputation of zero values using multiplicative replacement (Martin-Fernandez et al., 2003). The human gene data was transformed using a Yeo-Johnson power transformation.

C. Analysis

Both machine-learned models are Elastic Nets (EN: linear regression with tunable L1 and L2 regularization). We also tried other approaches including deep neural networks (DNN), random forest, Adaboost and a combination of metric learning and k-nearest neighbors. As results were similar across all approaches, we report the simplest model class.

Microbiome model. Hyperparameter optimization was done using a 5-fold Cross-validation on the discovery cohort. A final model using the optimal hyperparameter setting was then trained on the full discovery cohort and applied to the validation cohort to test generalization. Hyperparameter settings were scored using R2 and the selected model was evaluated using Mean Absolute Error (MAE) and R2.

Human gene model. Due to the smaller dataset size, model evaluation is performed using a nested CV. An inner 3-fold CV was used for hyperparameter selection while an outer 5-fold CV was used for model evaluation. Hyperparameter settings in each were scored using R2 and evaluated using MAE and R2.

Cohort comparisons. As an additional exploration of our stool microbiome model, we compare the biological age predicted for a number of specific subsets of the full microbiome dataset (discovery plus validation) corresponding to populations of interest. In each case we select all available samples from the population of interest (e.g. vegetarians), and create an appropriate control cohort (e.g. omnivores) where each member of the control cohort is matched on age to one member of the reference cohort. We perform a paired sample t-test to determine whether there is a significant difference in biological age between the cohorts. The cohorts consist of: people reporting the special diets vegan, vegetarian, organic, paleo, ketogenic (contrasted with people following no special diet); people with self-reported IBS, diabetes, depression or obesity (contrasted with people reporting no health issues); people reporting a sedentary lifestyle (contrasted with those not); heavy drinkers (contrasted with non-drinkers); heavy smokers (contrasted with non-smokers). Heavy drinkers were defined following Mayo Clinic guidelines as consuming 15 or more drinks per week for males and 8 or more for females. Smokers were defined as smoking a pack or more of cigarettes per day.

TABLE 1

Model performance by cohort.

| | Stool microbiome | | | | Human blood transcriptome |
|---|---|---|---|---|---|
| | Microbiome discovery cohort (cross-validated) | Validation cohort (prospective) | Matched cohort with CV in Galkin et al. | Matched cohort with HC in Galkin et al. | Blood transcriptome discovery cohort (cross-validated) |
| Cohort size | 78,637 | 11,666 | 1164 | 252 | 1494 |
| Sex (% female) | 64.10 | 65.37 | 64.95 | 48.41 | 61.29 |
| Age (y) means. d. | 46.79 15.9 | 43.22 15.75 | 49.00 15.35 | 48.06 11.36 | 47.24 14.22 |
| Baseline MAE | 12.98 | 12.90 | 13.03 | 9.36 | 11.75 |
| Prediction $R^2$ | 0.42 0.00 | 0.46 | 0.462 | 0.31 | 0.53 0.02 |
| Prediction MAE | 9.49 0.02 | 9.21 | 9.14 | 7.64 | 7.63 0.25 |

II. Results

A. Microbiome

FIG. 3 presents descriptive statistics of the discovery cohort. Ages of participants range from <1 years to 104 years, with 2686 participants below 18 years of age (included with parental consent). Study participants come from over 60 countries (86% US, 8% Canada, 3% Australia, rest from other countries). We do not observe any differences in taxonomic richness by age (FIG. 3b-c); nor do we find differences in taxonomic diversity or active function richness. None of these four measures were found to increase predictive accuracy when included in our models. FIG. 3d-e shows the species and KOs that vary the most with age. To identify these, we calculated the mean CLR for each feature in each decade of age in 70% of the discovery cohort, and chose those with the highest variance across ages. Then we plotted the trend in mean CLR by decade in the remaining 30% of the data, grouped by genus and KEGG hierarchy class. Notably, all of the KOs with the highest positive association with age are part of the KEGG methane metabolism pathway.

Figure 4A:
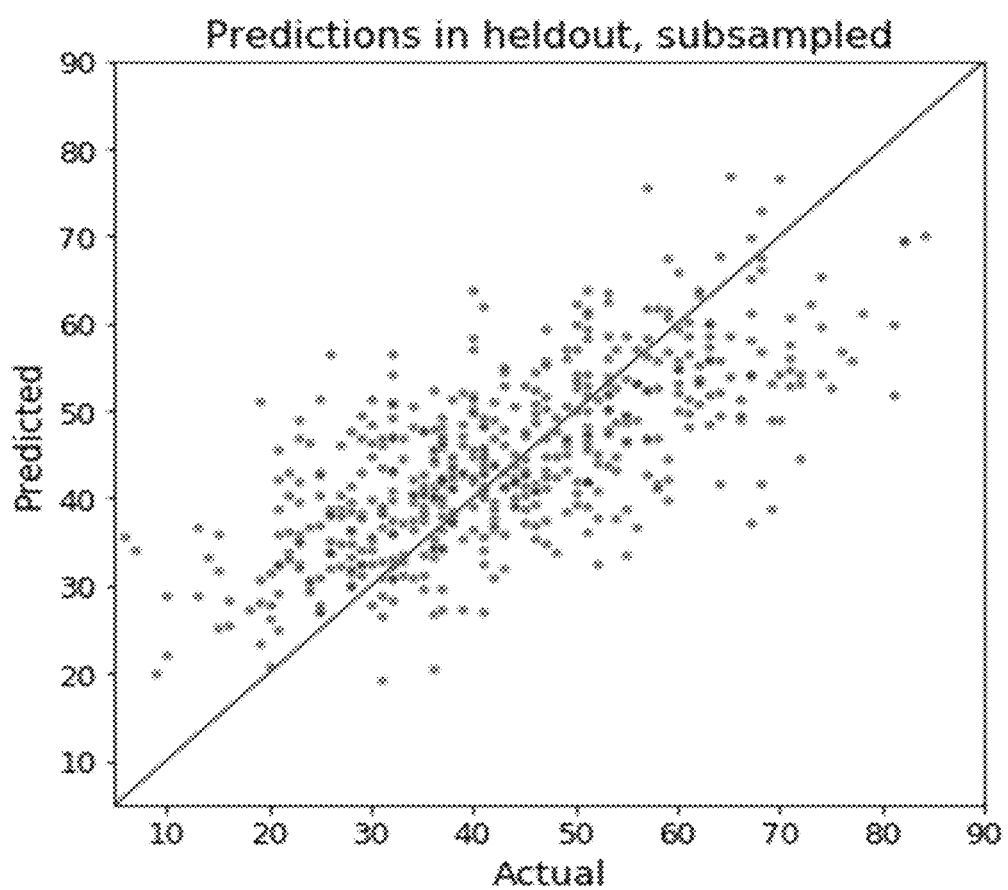
FIGS. 4A-4C show a predictive model using microbiome discovery cohort. (a) Predicted vs actual age in held-out validation data (for clarity, only a random subset of points is shown) (b) Coefficients for the taxa features with absolute coefficients >0.3 (c) Coefficients for the KO features with absolute coefficients >0.15. The size of the marker represents the mean expression level.
Figure 4B:
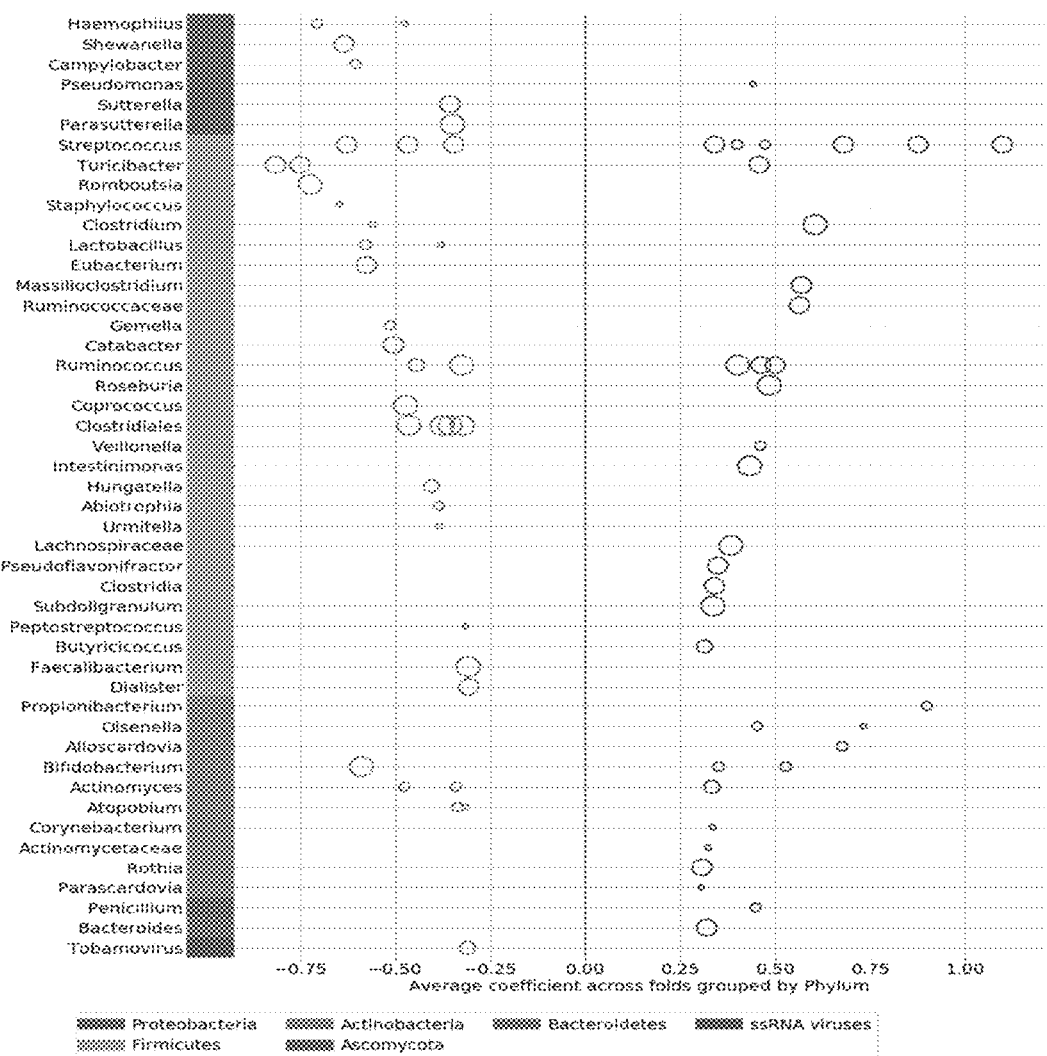
Figure 4C:
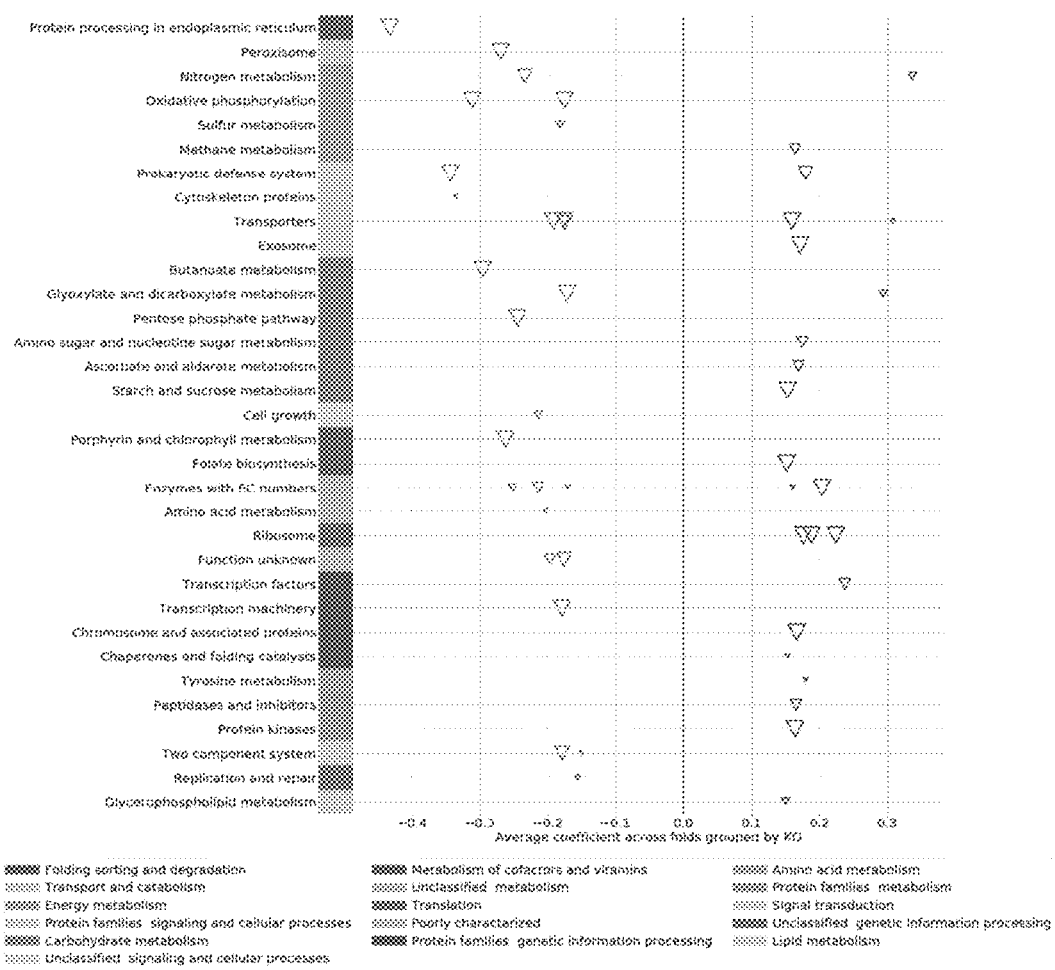

The biological age model's performance is presented in Table 1. The model predicts chronological age above the baseline MAE of the datasets, and accounts for over 40% of the variance in age by R2, the standard metric of quality of fit in regression tasks. Our biological age model's predictions and most important predictors shown in FIG. 4. FIGS. 4b and 4c show the features with highest absolute coefficients (above 0.3 for taxa and 0.15 for KOs), grouped by genus and phylum for taxa, and KEGG hierarchy levels 2 and 3 for KOs.

Figure 5A:
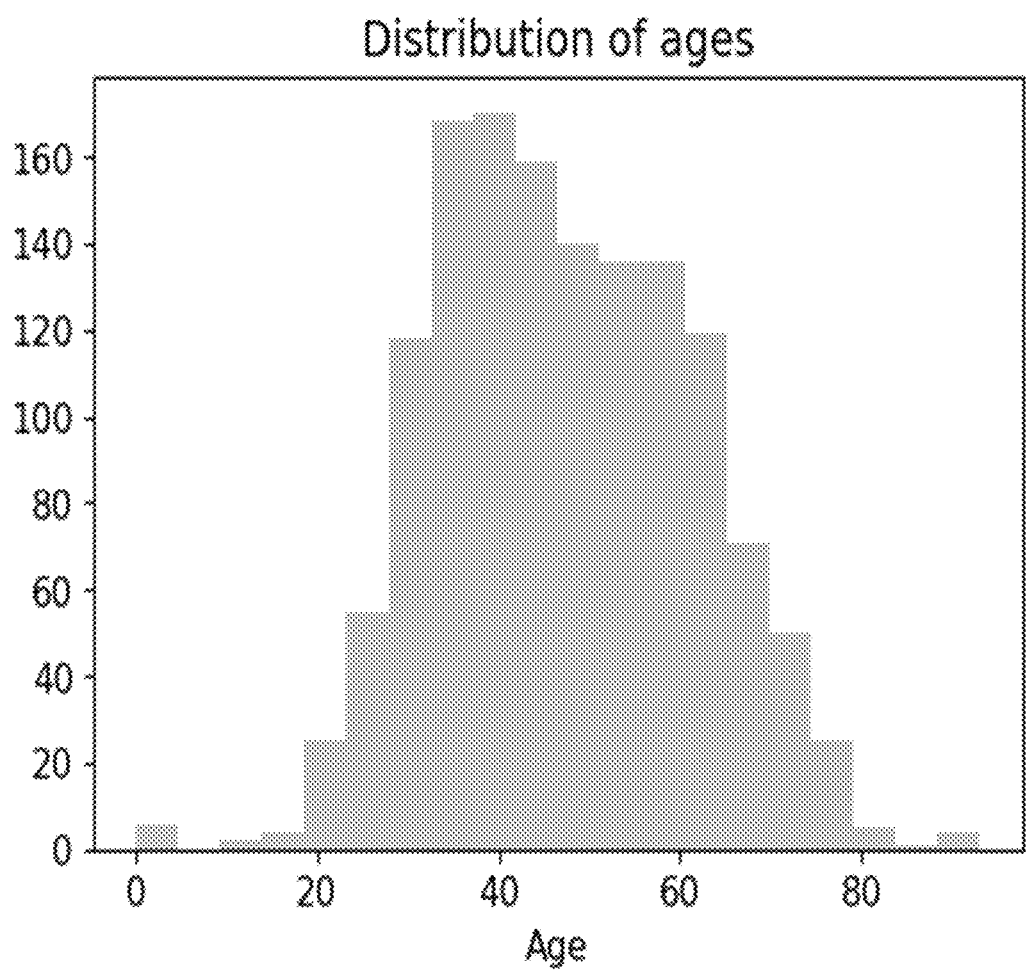
FIGS. 5A-5C show (a) Age distribution for HI samples, (b) Actual vs Predicted and (c) Features associated to large coefficients.
Figure 5B:
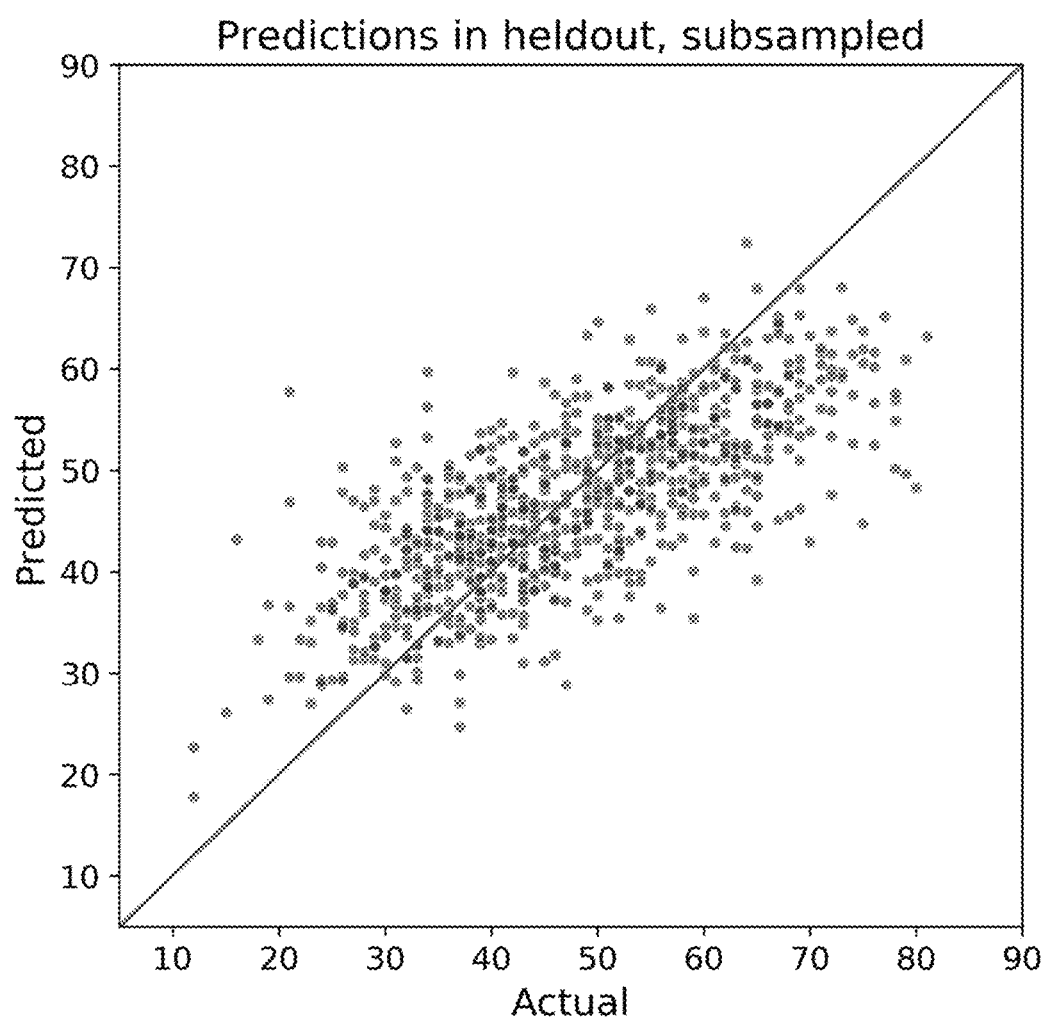
Figure 5C:
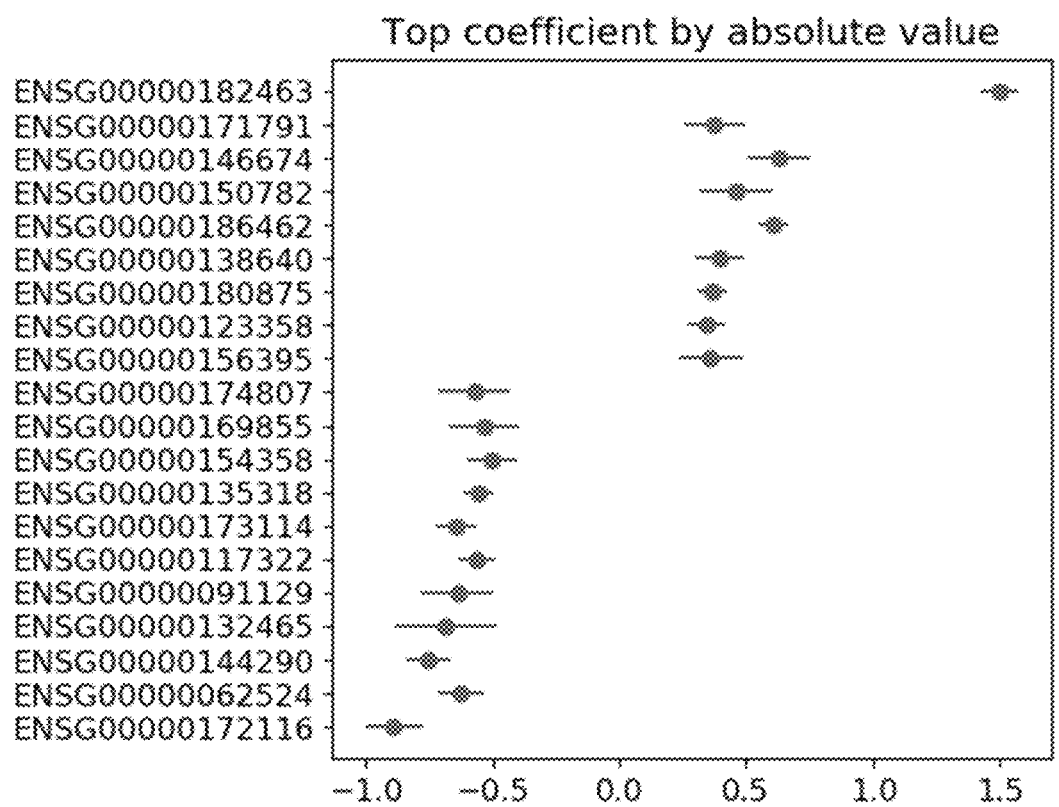

To explore the biological age of specific populations of interest, we present summaries of paired sample t-tests in FIG. 5a, which depicts the difference in mean biological ages for specific cohort comparisons of interest, together with p-values from corresponding t-tests. FIG. 5b shows the difference in chronological age for these same populations within the discovery cohort. We note that the model picks up several interesting differences between these populations and their age-matched controls. Vegetarians and vegans both tend to have a lower biological age than omnivores, while those following the ketogenic or paleo diets are biologically older than omnivores. Heavy drinkers are biologically older than non-drinkers, and smokers older than non-smokers. People with diabetes or IBS appear older than healthy controls, while those with depression appear younger.

B. Human Transcriptome

FIG. 6 presents the distribution of ages in the human cohort. Table 1 presents performance of the model under 5-fold cross validation. The model accounts for around 53% of variance in ages in the dataset.

C. Discussion

The models presented are capable of predicting chronological age above the baseline MAE of the datasets, and account for around 46% (microbiome) and 53% (stool) of the variance in age by $R^2$. We note that some discrepancy between predicted and actual age is expected in a useful biological age candidate.

Figure 6A:
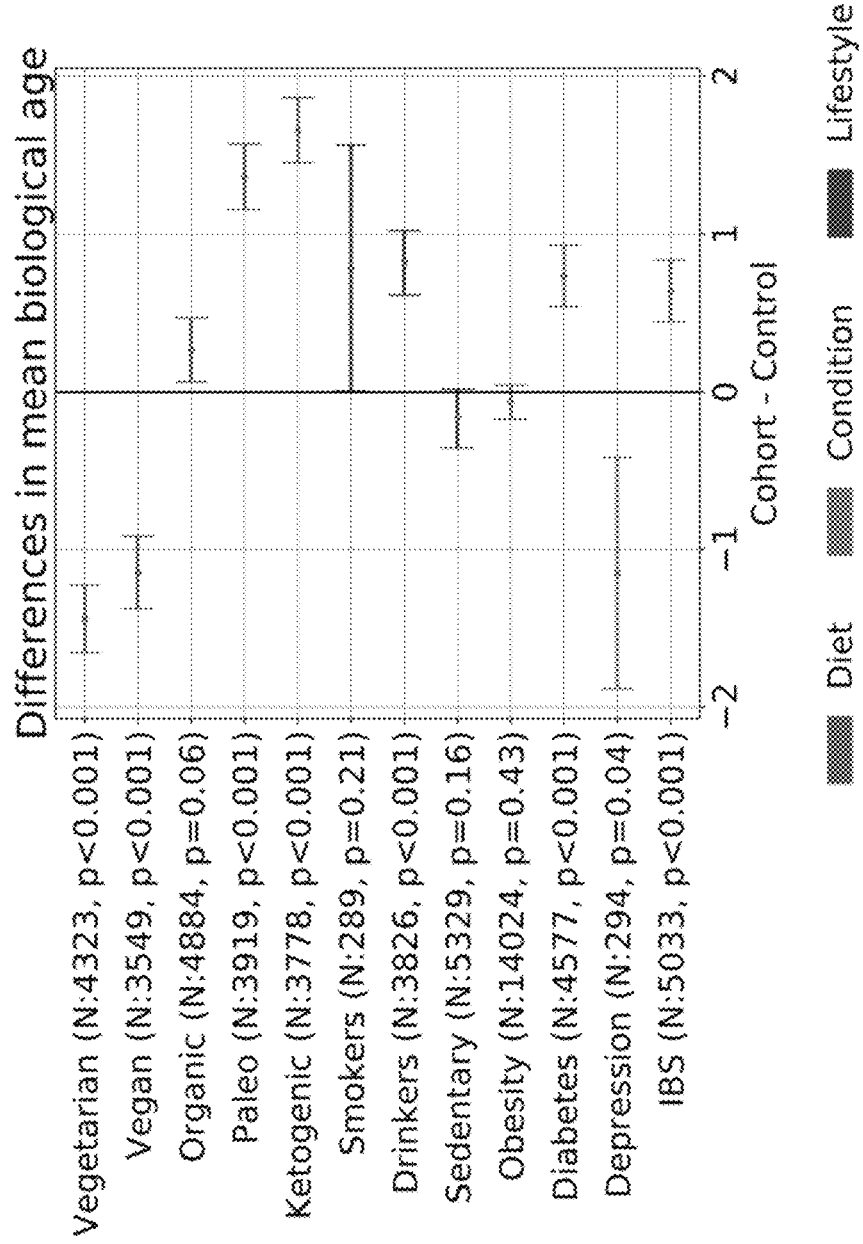
FIGS. 6A-6B show cohort comparisons: (a) Mean and standard error of biological age differences between cohorts and age-matched controls. p-values from paired t-tests. (b) Mean and standard error of chronological age differences between cohorts and controls in the discovery cohort.
Figure 6B:
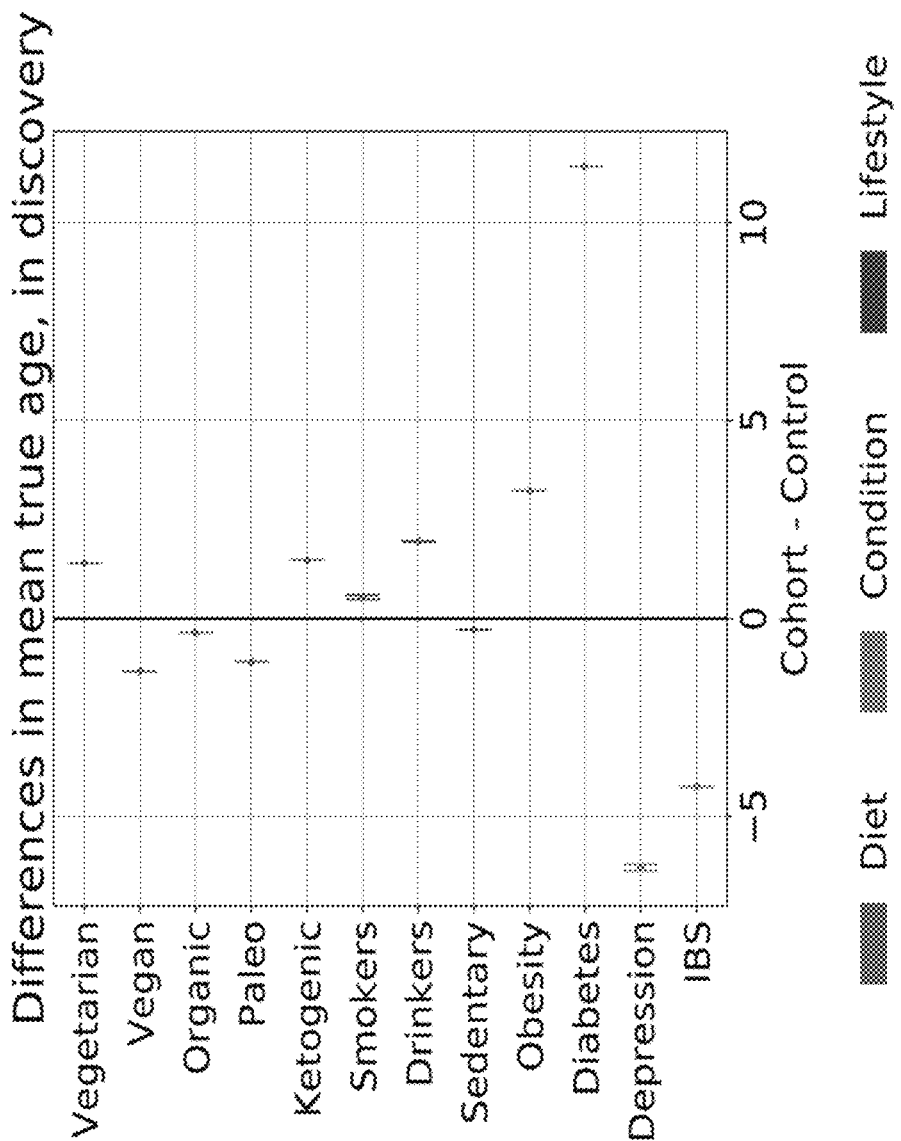

The trends in FIG. 6a show that several lifestyle choices widely understood to be healthy are associated with a lower biological age. For instance, those on plant-based diets appear younger (see review in Medawar et al., 2019) while smokers, drinkers, and IBS and diabetes sufferers appear older. The findings that those on a ketogenic or paleo diet appear older and those suffering from depression appear older is not expected, although there is relatively less prior reason to expect biological age differences in those cases. For some of these cohorts (e.g. drinking, depression, diabetes) the age distribution in the training data mirrors the predicted age (FIG. 6b). In these cases it is unclear whether the model has identified aspects of the microbiome that reflect general aging that are modulated in the groups of interest, or properties specific to the cases seen in training, as there is overlap between the discovery cohort and these cohorts. However for other cohorts (e.g. vegetarians, paleo, IBS) the opposite pattern is seen, which strongly suggests that the microbiome features associated with these populations include features associated with aging in the general population. Overall, these results are consistent with an interpretation of our biological age metric as reflecting an accumulation of lifestyle choices and disease status that contribute to healthy aging.

The resolution of the data supplied by our next-generation sequencing approach allows identification of organisms at the strain level, although for this analysis we aggregate data to the species level. This contrasts with 16S gene sequencing, which does not discriminate between species within most genera. This additional resolution appears to be important to capture variation associated with age. For example, among the most important model features shown in FIG. 2b, there are *Clostridium* species associated with older people, and others associated with younger people.

Of the most significant features associated with older age, many are known as oral commensals or oral pathogens, which are found in saliva, gingival or subgingival plaques, and other sites from the oral cavity. The four most important *Streptococcus* species, the Actinomycetaceae species and the *Alloscardovia* species have previously been detected as a normal component of the oral microbiome and implicated in pro-inflammatory processes during oral dysbiosis (Nagata et al., 2011; Aas et al., 2005). Presence and activity of oral taxa in the gut is an established marker of hypochlorhydria (low stomach acid), which is known to develop with age as stomach acid levels and digestive efficiency progressively decline (Martinsen et al., 2005; Banoo et al., 2016; D'Souza, 2007). The top gene-encoded function associated with younger age is a heat shock protein involved in protein folding. Although not previously directly documented in association with human aging via the gut microbiome, heat shock proteins and the protein folding machinery generally decline and become less efficient with age (Edwards, 2011; Calderwood, 2009).

REFERENCES

Aitchison J. The Statistical Analysis of Compositional Data. (1986); Chapman and Hall.

Aas, Jørn A., Bruce J. Paster, Lauren N. Stokes, Ingar Olsen, and Floyd E. Dewhirst. Defining the Normal Bacterial Flora of the Oral Cavity. Journal of Clinical Microbiology 43, no. 11 (November 2005): 5721-32. doi:10.1128/JCM.43.11.5721-5732.2005.

Banoo, H. and Nusrat, N. Implications of Low Stomach Acid: An Update RAMA Univ. J. Med Sci (2016); 2(2): 16-26

Bell, C. G., Lowe, R., Adams, P. D. et al. DNA methylation aging clocks: challenges and recommendations. Genome Biol (2019); 20, 249. doi:10.1186/s13059-019-1824-y Breitwieser, F. P., Lu, J., Salzberg, S. L., A review of methods and databases for metagenomic classification and assembly, Briefings in Bioinformatics, 20(4), 1125-1136, doi:10.1093/bib/bbx120

Calderwood, S. K., Murshid, A., and Prince, T. The Shock of Aging: Molecular Chaperones and the Heat Shock Response in Longevity and Aging—A Mini-Review. Gerontology. 2009 September; 55(5): 550-558.

de la Cuesta-Zuluaga J., Kelley S. T., Chen Y., Escobar J. S., Mueller N. T., Ley R. E., McDonald D., Huang S., Swafford A. D., Knight R, Thackray V. G., Age- and sex-dependent patterns of gut microbial diversity in human adults. mSystems. 2019; 4:e00261-19. doi: 10.1128/mSystems.00261-19

Dempster, A. P., N. M. Laird and D. B. Rubin. Maximum likelihood from incomplete data via the E M algorithm. Journal of the Royal Statistical Society. (1977); Series B. (29), 1-37.

D'Souza, A L. Aging and the Gut. Postgraduate Medical Journal 83, no. 975 (2007): 44-53. doi:10.1136/pgmj.2006.049361.

Earls, J. C., Rappaport, N., Heath, L, Wilmanski, T., Magis, A. T., Schork, N. J., Omenn, G. S., Lovejoy, J., Hood, L., Price, N. D., Multi-Omic Biological Age Estimation and Its Correlation With Wellness and Disease Phenotypes: A Longitudinal Study of 3,558 Individuals, The Journals of Gerontology. (2019); 52-S60, doi:10.1093/gerona/glz220

Edwards, H. V., Cameron, R. T and Baillie, G. S. The Emerging Role of HSP20 as a Multifunctional Protective Agent. Cell Signal. (2011); 23(9), 1447-54.

Fraga, M. F., and Esteller, M. Epigenetics and aging: the targets and the marks. Trends Genet. (2007); 23, 413-418.

Galkin, F., Mamoshina, P., Aliper, A., Putin, E., Moskalev, V., Gladyshev, V. N., Zhavoronkov, A. Human gut microbiome aging clock based on taxonomic profiling and deep learning, ISCIENCE (2020); doi:10.1016/j.isci.2020.101199.

Ghosh T. S., Rampelli S., Jeffery I. B., et al. Mediterranean diet intervention alters the gut microbiome in older people reducing frailty and improving health status: the NU-AGE 1-year dietary intervention across five European countries. Gut (2019); doi: 10.1136/gutjnl-2019-319654

Harries L W, Hernandez D, Henley W, et al. Human aging is characterized by focused changes in gene expression and deregulation of alternative splicing. Aging Cell. (2011); 10(5):868-878. doi:10.1111/j.1474-9726.2011.00726.x Holly A. C., Melzer D., Pilling L. C., et al. Towards a gene expression biomarker set for human biological age. Aging Cell. (2013); 12(2):324-326. doi:10.1111/acel.12044

Hopkins M. J., Sharp R., Macfarlane G. T., 2002. Variation in human intestinal microbiota with age. Dig Liver Dis 34 (Suppl 2):512-518. doi:10.1016/51590-8658(02)80157-8.

Horvath, S., & Raj, K. DNA methylation-based biomarkers and the epigenetic clock theory of aging. Nature Reviews Genetics (2018); 19, 371-384.

Jia L, Zhang W, Chen X. Common methods of biological age estimation. Clin Interv Aging. (2017); 12:759-772. doi:10.2147/CIA.S134921

Kanehisa, M., Goto, S., KEGG: Kyoto Encyclopedia of Genes and Genomes, Nucleic Acids Research. (2000); 28(1), 27-30, doi:10.1093/nar/28.1.27

Kim S. & Jazwinski S. M. The gut microbiota and healthy aging: A mini-review. Gerontology (2018); 64:513-520. do:10.1159/000490615

Koenig J. E., Spor A., Scalfone N., Fricker A. D., Stombaugh J., Knight R., Angenent L. T., Ley R. E. 2011. Succession of microbial consortia in the developing infant gut microbiome. Proc Natl Acad Sci USA 108 (Suppl 1):4578-4585. doi:10.1073/pnas.1000081107.

Lin H., Lunetta K. L., Zhao Q., et al. Whole Blood Gene Expression Associated With Clinical Biological Age. J Gerontol A Biol Sci Med Sci. (2019); 74(1):81-88. doi: 10.1093/gerona/gly164

Mariat D., Firmesse O., Levenez F., Guimarães V., Sokol H., Doré J., Corthier G., Furet J P. 2009. The Firmicutes/Bacteroidetes ratio of the human microbiota changes with age. BMC Microbiol 9:123. doi:10.1186/1471-2180-9-123.

Martin-Fernández, J. A., Barceló-Vidal, C. & Pawlowsky-Glahn, V. Dealing with zeros and missing values in compositional data sets using nonparametric imputation. Mathematical Geology. (2003); 35, 253-278. doi:10.1023/A:1023866030544

Maffei V. J., Kim S., Blanchard E. 4th, et al. Biological aging and the human gut microbiota. J Gerontol A Biol Sci Med Sci. (2017); 72(11):1474-1482. doi:10.1093/gerona/glx042

Mamoshina P., Kochetov K., Putin E., et al. Population specific biomarkers of human aging: A big data study using South Korean, Canadian, and Eastern European patient populations. J Gerontol A Biol Sci Med Sci. (2018); 73(11): 1482-1490. doi:10.1093/gerona/gly005

Mamoshina P., Volosnikova, M., Ozerov, I. V., Putin, E. Skibina, E., Cortese, F., Zhavoronkov, A. Machine learning on human muscle transcriptomic data for biomarker discovery and tissue-specific drug target identification. Front. Genet. (2018); 9: 242

Martinsen, Tom C., Kåre Bergh, and Helge L. Waldum. Gastric Juice: A Barrier Against Infectious Diseases. Basic & Clinical Pharmacology & Toxicology 96, no. 2 (2005): 94-102. doi:10.1111/j.1742-7843.2005.pto960202.x.

Medawar, E., Huhn, S., Villringer, A. et al. The effects of plant-based diets on the body and the brain: a systematic review. Transl Psychiatry 9, 226 (2019). doi:10.1038/s41398-019-0552-0

Nagata, E., A. de Toledo, and T. Oho. Invasion of Human Aortic Endothelial Cells by Oral Viridans Group Streptococci and Induction of Inflammatory Cytokine Production. Molecular Oral Microbiology 26, no. 1 (2011):78-88. doi:10.1111/j.2041-1014.2010.00597.x.

Patro, R., Duggal, G., Love, M. et al. Salmon provides fast and bias-aware quantification of transcript expression. Nat. Methods, (2017); 14: 417-419. doi:10.1038/nmeth.4197

Pyrkov T. V., Slipensky K., Barg M., et al. Extracting biological age from biomedical data via deep learning: too much of a good thing?. Sci Rep. (2018); 8(1):5210. doi:10.1038/s41598-018-23534-9

Sae-Lee C., Corsi S., Barrow T. M., et al. Dietary Intervention Modifies DNA Methylation Age Assessed by the Epigenetic Clock. Mol Nutr Food Res. (2018); 62(23): e1800092. doi:10.1002/mnfr.201800092

Toma, R., Duval, N., Pelle, N., Parks, M. M., Gopu, V., Torres, P. J., Camacho, F. R., Tily, H., Hatch, A., Perlina, A., Banavar, G., and Vuyisich, M., A clinically-validated human capillary blood transcriptome test for global systems biology studies. Manuscript under review. doi: 10.1101/2020.05.22.110080

Wang, M., & Lemos, B. Ribosomal DNA harbors an evolutionarily conserved clock of biological aging. Genome Res. (2019); doi:10.1101/gr.241745.118

Watson, M. M & Søreide, K. The Gut Microbiota influence on human epigenetics, health, and disease. Handbook of Epigenetics (2nd ed.) (2017); Academic Press. chap. 32, 495-510.

Yatsunenko T., Rey F. E., Manary M. J., Trehan I., Dominguez-Bello M. G., Contreras M., Magris M., Hidalgo G., Baldassano R. N., Anokhin A. P., Heath A. C., Warner B., Reeder J., Kuczynski J., Caporaso J. G., Lozupone C. A., Lauber C., Clemente J. C., Knights D., Knight R., Gordon J. I. 2012. Human gut microbiome viewed across age and geography. Nature 486:222-227. doi:10.1038/nature11053

Galkin et al. also report MAE of 5.91 for this dataset but note that the data contains multiple samples from many of the subjects, and after merging duplicates into averaged samples, performance falls to 6.85. As performance on averaged samples is not representative of performance on individual samples, we report metrics for the Galkin et al. model after randomly excluding all but one sample from each donor. The metrics we report here are calculated from the predictions for individual samples shared as part of that paper's supplementary data.

ENSG00000171791 is BCL2 apoptosis regulator whose protein expression also showed age-associated differences. Available on the Internet at journals.physiology.org/doi/full/10.1152/ajpregu.1998.275.1. R315-cool.

As used herein, the following meanings apply unless otherwise specified. The word "may" is used in a permissive sense (i.e., meaning having the potential to), rather than the mandatory sense (i.e., meaning must). The words "include", "including", and "includes" and the like mean including, but not limited to. The singular forms "a," "an," and "the" include plural referents. Thus, for example, reference to "an element" includes a combination of two or more elements, notwithstanding use of other terms and phrases for one or more elements, such as "one or more." The phrase "at least one" includes "one", "one or more", "one or a plurality" and "a plurality". The term "or" is, unless indicated otherwise, non-exclusive, i.e., encompassing both "and" and "or." The term "any of" between a modifier and a sequence means that the modifier modifies each member of the sequence. So, for example, the phrase "at least any of 1, 2 or 3" means "at least 1, at least 2 or at least 3". The term "consisting essentially of" refers to the inclusion of recited elements and other elements that do not materially affect the basic and novel characteristics of a claimed combination.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

All publications, patents, and patent applications mentioned in this specification are herein incorporated by reference to the same extent as if each individual publication, patent, or patent application was specifically and individually indicated to be incorporated by reference.

What is claimed is:

1. A method for inferring biological age in a subject, comprising:
   at a computer system comprising at least one processor and a memory storing at least one program for execution by the at least one processor:
   a) obtaining first sequence information in electronic form for a first plurality of nucleic acids, wherein the first plurality of nucleic acids comprises 10,000 or more sequences representing a microbiome of a subject, and wherein the first plurality of nucleic acids are from a first biological sample of the subject;
   b) determining, from the first sequence information, a respective measure of transcriptional activity for each respective microbial taxa in a plurality of microbial taxa, wherein:
      the plurality of microbial taxa comprises at least 5 taxa selected from *Streptococcus gordonii*, *Propionibacterium acidifaciens*, *Streptococcus mutans*, *Olsenella profusa*, *Streptococcus vestibularis*, *Alloscardovia omnicolens*, *Clostridium phoceensis*, *Massilioclostridium coli*, Ruminococcaceae bacterium Marseille-P2963, *Bifidobacterium dentium*, *Ruminococcus gauvreauii*, *Roseburia intestinalis*, *Streptococcus* sp. HMSC10A01, *Ruminococcus* sp. AT10, *Veillonella atypica*, *Turicibacter* sp. HGF1, *Olsenella uli*, *Penicillium digitatum*, *Pseudomonas aeruginosa*, *Intestinimonas butyriciproducens*, *Ruminoccoccus* sp. Marseille-P3213, *Streptococcus* sp. CCH8-G7, Lachnospiraceae bacterium TF01-11, *Bifidobacterium* sp. MSTE12, *Pseudoflavonifractor capillosus*, *Streptococcus parasanguinis*, Clostridia bacterium UC5 1-1E11, *Subdoligranulum* sp 4_3_54A2FAA, *Corynebacterium matruchotii*, *Actinomyces dentalis*, Actinomycetaceae bacterium BA112, *Bacteroides* sp. HPS0048, *Butyricicoccus pullicaecorum*, *Rothia mucilaginosa*, *Parascardovia denticolens*, *Dialister invisus*, *Faecalibacterium prausnitzii*, Tobacco mild green mosaic virus, *Peptostreptococcus stomatis*, *Atopobium* sp. HMSC064B08, *Clostridiales bacterium*, *Ruminococcus faecis*, *Atopobium rimae*, *Actinomyces* sp. oral taxon 181, *Streptococcus intermedius*, *Parasutterella excrementihominis*, *Sutterella wadsworthensis*, *Lactobacillus iners*, *Urmitella timonensis*, *Abiotrophia* sp. HMSC24B09, *Hungatella hathewayi*, *Ruminococcus* sp. DSM 100440, *Streptococcus* sp. F0442, *Coprococcus eutactus*, *Haemophilus sputorum*, *Actinomyces gerencseriae*, *Catabacter hongkongensis*, *Gemella morbillorum*, *Clostridium ventriculi*, *Eubacterium* sp. 3_1_31, *Lactobacillus crispatus*, *Bifidobacterium longum*, *Campylobacter hominis*, *Streptococcus anginosus*, *Shewanella colwelliana*, *Staphylococcus aureus*, *Haemophilus pittmaniae*, *Romboutsia timonensis*, *Turicibacter sanguinis*, and *Turicibacter* sp. H121, and
      the respective measure is obtained by matching each respective nucleic acid in the first plurality of nucleic acids to individual sequences of the plurality of taxa;
   c) obtaining second sequence information in electronic form for a second plurality of nucleic acids, wherein the second plurality of nucleic acids comprises 10,000 or more sequences representing a transcriptome of the subject, and wherein the second plurality of nucleic acids are from a second biological sample of the subject;

d) determining, from the second sequence information, a respective measure of transcriptional activity for each respective KEGG ortholog definition in a plurality of KEGG ortholog definitions as an abundance of nucleic acids encoding the respective KEGG ortholog, wherein:

the plurality of KEGG ortholog definitions includes at least 5 KEGG ortholog definitions selected from ferredoxin-nitrite reductase, cytochrome c-type biogenesis protein Ccmf, methylaspartate ammonia-lyase, AraC family transcriptional regulator, small subunit ribosomal protein S20, oleate hydratase, small subunit ribosomal protein S16, type III restriction enzyme, tyrosine phenol-lyase, large subunit ribosomal protein L19, CDP-4-dehydro-6-deoxyglucose reductase E1, peroxiredoxin 2/4, L-ascorbate 6-phosphate lactonase, starvation-inducible DNA-binding protein, spore protease, serine/threonine-protein kinase HipA, methanol-5-hydroxybenzimidazolylcobamide co-methyltransferase, opine dehydrogenase, ferrous iron transport protein A, beta-glucosidase, molecular chaperone IbpB, dihydrofolate reductase, glycerol-3-phosphate dehydrogenase subunit B, two-component system OmpR family phosphate regulon response regulator OmpR, putative transposase, fructoselysine 6-phosphate deglycase, propionyl CoA carboxylase beta chain, OmpA-OmpF porin OOP family, F-type H+ transporting ATPase subunit B, iron complex transport system substrate-binding protein, translocator protein, accessory gene regulator B, RNA polymerase sigma 70 factor ECF subfamily, anaerobic dimethyl sulfoxide reductase subunit B, putative ABC transport system ATP-binding protein, D-proline reductase (dithiol) stabilizing protein PrdE, fructoselysine 4-epimerase, stage V sporulation protein AC, glutamate synthase (NADPH) large chain, 6-phosphogluconate dehydrogenase, aryl-sulfate sulfotransferase, sirohydrochlorin cobaltochelatase, superoxide dismutase Fe—Mn family, glutamate decarboxylase, F-type H+/Na+ transporting ATPase subunit beta, actin, mRNA interferase MazF, and HSP20 family protein, and the respective measure is obtained by matching each respective nucleic acid in the second plurality of nucleic acids to individual sequences of the plurality of KEGG ortholog definitions; and e) inputting into a model (i) the respective measure of transcriptional activity for each respective microbial taxa in the plurality of microbial taxa and (ii) the respective measure of transcriptional activity for each respective KEGG ortholog definition in the plurality of KEGG ortholog definitions, to obtain as output from the model a biological age of the subject.

2. The method of claim 1, further comprising:
f) outputting the biological age of the subject to a user interface device or the memory.

3. The method of claim 1, further comprising:
f) delivering and/or administering to the subject a therapeutic intervention effective to alter a rate of biological aging.

4. The method of claim 1, wherein the subject is a human or non-human animal.

5. The method of claim 1, wherein the second biological sample is a somatic cell sample.

6. The method of claim 5, wherein the first sample comprises feces and the somatic cell sample comprises blood or a blood fraction.

7. The method of claim 5, wherein the first sample is a gut microbiome sample and the somatic cell sample is a leukocyte sample.

8. The method of claim 1, wherein the first plurality of nucleic acids comprises a microbiome metatranscriptome and the second plurality of nucleic acids comprises a somatic cell metatranscriptome.

9. The method of claim 1, wherein the plurality of microbial taxa comprises at least one of *Streptococcus gordonii, Propionibacterium acidifaciens, Streptococcus mutans, Turicibacter* sp. H121, *Turicibacter sanguinis, Olsenella profuse, Romboutsia timonensis, Haemophilus pittmaniae, Streptococcus vestibularis*, and *Alloscardovia omnicolens*.

10. The method of claim 1, wherein:
the plurality of microbial taxa consists of taxa selected from *Streptococcus gordonii, Propionibacterium acidifaciens, Streptococcus mutans, Olsenella profuse, Streptococcus vestibularis, Alloscardovia omnicolens, Clostridium phoceensis, Massilioclostridium coli,* Ruminococcaceae bacterium Marseille-P2963, *Bifidobacterium dentium, Ruminococcus gauvreauii, Roseburia intestinalis, Streptococcus* sp. HMSC10A01, *Ruminococcus* sp. AT10, *Veillonella atypica, Turicibacter* sp. HGF1, *Olsenella uli, Penicillium digitatum, Pseudomonas aeruginosa, Intestinimonas butyriciproducens, Ruminoccuccus* sp. Marseille-P3213, *Streptococcus* sp. CCH8-G7, Lachnospiraceae bacterium TF01-11, *Bifidobacterium* sp. MSTE12, *Pseudoflavonifractor capillosus, Streptococcus parasanguinis, Clostridia bacterium* UC5 1-1E11, *Subdoligranulum* sp 4_3_54A2FAA, *Corynebacterium matruchotii, Actinomyces dentalis,* Actinomycetaceae bacterium BA112, *Bacteroides* sp. HPS0048, *Butyricicoccus pullicaecorum, Rothia mucilaginosa, Parascardovia denticolens, Dialister invisus, Faecalibacterium prausnitzii,* Tobacco mild green mosaic virus, *Peptostreptococcus stomatis, Atopobium* sp. HMSC064B08, *Clostridiales bacterium, Ruminococcus faecis, Atopobium rimae, Actinomyces* sp. oral taxon 181, *Streptococcus intermedius, Parasutterella excrementihominis, Sutterella wadsworthensis, Lactobacillus iners, Urmitella timonensis, Abiotrophia* sp. HMSC24B09, *Hungatella hathewayi, Ruminococcus* sp. DSM 100440, *Streptococcus* sp. F0442, *Coprococcus eutactus, Haemophilus sputorum, Actinomyces gerencseriae, Catabacter hongkongensis, Gemella morbillorum, Clostridium ventriculi, Eubacterium* sp. 3_1_31, *Lactobacillus crispatus, Bifidobacterium longum, Campylobacter hominis, Streptococcus anginosus, Shewanella colwelliana, Staphylococcus aureus, Haemophilus pittmaniae, Romboutsia timonensis, Turicibacter sanguinis,* and *Turicibacter* sp. H121, and the plurality of KEGG ortholog definitions consists of KEGG ortholog definitions selected from ferredoxin-nitrite reductase, cytochrome c-type biogenesis protein Ccmf, methylaspartate ammonia-lyase, AraC family transcriptional regulator, small subunit ribosomal protein S20, oleate hydratase, small subunit ribosomal protein S16, type III restriction enzyme, tyrosine phenol-lyase, large subunit ribosomal protein L19, CDP-4-dehydro-6-deoxyglucose reductase E1, peroxiredoxin 2/4, L-ascorbate 6-phosphate lactonase, starvation-inducible DNA-binding protein, spore protease, serine/threonine-protein kinase HipA, methanol-5-hydroxybenzimidazolylcobamide co-methyltransferase, opine dehydrogenase, ferrous iron transport protein A, beta-glucosidase, molecular chaperone IbpB, dihydrofolate reductase, glycerol-3-phosphate dehydrogenase subunit B, two-component system OmpR family phosphate regulon response regulator OmpR, putative transposase, fructoselysine 6-phosphate deglycase, propionyl CoA carboxylase beta chain, OmpA-OmpF porin OOP family, F-type H+ transporting ATPase subunit B, iron complex transport system substrate-binding protein, translocator protein, accessory gene regulator B, RNA polymerase sigma 70 factor ECF subfamily, anaerobic dimethyl sulfoxide reductase subunit B, putative ABC transport system ATP-binding protein, D-proline reductase (dithiol) stabilizing protein PrdE, fructoselysine 4-epimerase, stage V sporulation protein AC, glutamate synthase (NADPH) large chain, 6-phosphogluconate dehydrogenase, aryl-sulfate sulfotransferase, sirohydrochlorin cobaltochelatase, superoxide dismutase Fe—Mn family, glutamate decarboxylase, F-type H+/Na+ transporting ATPase subunit beta, actin, mRNA interferase MazF, and HSP20 family protein.

11. The method of claim 1, wherein the model uses an elastic net regression algorithm, a deep neural network, a random forest, or k-nearest neighbors.

12. The method of claim 1, wherein
the plurality of microbial taxa comprises at least 10 taxa selected from *Streptococcus gordonii, Propionibacterium acidifaciens, Streptococcus mutans, Olsenella profuse, Streptococcus vestibularis, Alloscardovia omnicolens, Clostridium phoceensis, Massilioclostridium coli*, Ruminococcaceae bacterium Marseille-P2963, *Bifidobacterium dentium, Ruminococcus gauvreauii, Roseburia intestinalis, Streptococcus* sp. HMSC10A01, *Ruminococcus* sp. AT10, *Veillonella atypica, Turicibacter* sp. HGF1, *Olsenella uli, Penicillium digitatum, Pseudomonas aeruginosa, Intestinimonas butyriciproducens, Ruminoccoccus* sp. Marseille-P3213, *Streptococcus* sp. CCH8-G7, Lachnospiraceae bacterium TF01-11, *Bifidobacterium* sp. MSTE12, *Pseudoflavonifractor capillosus, Streptococcus parasanguinis, Clostridia bacterium* UC5 1-1E11, *Subdoligranulum* sp 4_3_54A2FAA, *Corynebacterium matruchotii, Actinomyces dentalis*, Actinomycetaceae bacterium BA112, *Bacteroides* sp. HPS0048, *Butyricicoccus pullicaecorum, Rothia mucilaginosa, Parascardovia denticolens, Dialister invisus, Faecalibacterium prausnitzii*, Tobacco mild green mosaic virus, *Peptostreptococcus stomatis, Atopobium* sp. HMSC064B08, *Clostridiales bacterium, Ruminococcus faecis, Atopobium rimae, Actinomyces* sp. oral taxon 181, *Streptococcus intermedius, Parasutterella excrementihominis, Sutterella wadsworthensis, Lactobacillus iners, Urmitella timonensis, Abiotrophia* sp. HMSC24B09, *Hungatella hathewayi, Ruminococcus* sp. DSM 100440, *Streptococcus* sp. F0442, *Coprococcus eutactus, Haemophilus sputorum, Actinomyces gerencseriae, Catabacter hongkongensis, Gemella morbillorum, Clostridium ventriculi, Eubacterium* sp. 3_1_31, *Lactobacillus crispatus, Bifidobacterium longum, Campylobacter hominis, Streptococcus anginosus, Shewanella colwelliana, Staphylococcus aureus, Haemophilus pittmaniae, Romboutsia timonensis, Turicibacter sanguinis*, and *Turicibacter* sp. H121, and the plurality of KEGG ortholog definitions includes at least 10 KEGG ortholog definitions selected from ferredoxin-nitrite reductase, cytochrome c-type biogenesis protein Ccmf, methylaspartate ammonia-lyase, AraC family transcriptional regulator, small subunit ribosomal protein S20, oleate hydratase, small subunit ribosomal protein S16, type III restriction enzyme, tyrosine phenol-lyase, large subunit ribosomal protein L19, CDP-4-dehydro-6-deoxyglucose reductase E1, peroxiredoxin 2/4, L-ascorbate 6-phosphate lactonase, starvation-inducible DNA-binding protein, spore protease, serine/threonine-protein kinase HipA, methanol-5-hydroxybenzimidazolylcobamide co-methyltransferase, opine dehydrogenase, ferrous iron transport protein A, beta-glucosidase, molecular chaperone IbpB, dihydrofolate reductase, glycerol-3-phosphate dehydrogenase subunit B, two-component system OmpR family phosphate regulon response regulator OmpR, putative transposase, fructoselysine 6-phosphate deglycase, propionyl CoA carboxylase beta chain, OmpA-OmpF porin OOP family, F-type H+ transporting ATPase subunit B, iron complex transport system substrate-binding protein, translocator protein, accessory gene regulator B, RNA polymerase sigma 70 factor ECF subfamily, anaerobic dimethyl sulfoxide reductase subunit B, putative ABC transport system ATP-binding protein, D-proline reductase (dithiol) stabilizing protein PrdE, fructoselysine 4-epimerase, stage V sporulation protein AC, glutamate synthase (NADPH) large chain, 6-phosphogluconate dehydrogenase, aryl-sulfate sulfotransferase, sirohydrochlorin cobaltochelatase, superoxide dismutase Fe—Mn family, glutamate decarboxylase, F-type H+/Na+ transporting ATPase subunit beta, actin, mRNA interferase MazF, and HSP20 family protein.

13. The method of claim 1, wherein
the plurality of microbial taxa comprises at least 20 taxa selected from *Streptococcus gordonii, Propionibacterium acidifaciens, Streptococcus mutans, Olsenella profuse, Streptococcus vestibularis, Alloscardovia omnicolens, Clostridium phoceensis, Massilioclostridium coli*, Ruminococcaceae bacterium Marseille-P2963, *Bifidobacterium dentium, Ruminococcus gauvreauii, Roseburia intestinalis, Streptococcus* sp. HMSC10A01, *Ruminococcus* sp. AT10, *Veillonella atypica, Turicibacter* sp. HGF1, *Olsenella uli, Penicillium digitatum, Pseudomonas aeruginosa, Intestinimonas butyriciproducens, Ruminoccoccus* sp. Marseille-P3213, *Streptococcus* sp. CCH8-G7, Lachnospiraceae bacterium TF01-11, *Bifidobacterium* sp. MSTE12, *Pseudoflavonifractor capillosus, Streptococcus parasanguinis, Clostridia bacterium* UC5 1-1E11, *Subdoligranulum* sp 4_3_54A2FAA, *Corynebacterium matruchotii, Actinomyces dentalis*, Actinomycetaceae bacterium BA112, *Bacteroides* sp. HPS0048, *Butyricicoccus pullicaecorum, Rothia mucilaginosa, Parascardovia denticolens, Dialister invisus, Faecalibacterium prausnitzii*, Tobacco mild green mosaic virus, *Peptostreptococcus stomatis, Atopobium* sp. HMSC064B08, *Clostridiales bacterium, Ruminococcus faecis, Atopobium rimae, Actinomyces* sp. oral taxon 181, *Streptococcus intermedius, Parasutterella excrementihominis, Sutterella wadsworthensis, Lacto-

*bacillus iners, Urmitella timonensis, Abiotrophia* sp. HMSC24B09, *Hungatella hathewayi, Ruminococcus* sp. DSM 100440, *Streptococcus* sp. F0442, *Coprococcus eutactus, Haemophilus sputorum, Actinomyces gerencseriae, Catabacter hongkongensis, Gemella morbillorum, Clostridium ventriculi, Eubacterium* sp. 3_1_31, *Lactobacillus crispatus, Bifidobacterium longum, Campylobacter hominis, Streptococcus anginosus, Shewanella colwelliana, Staphylococcus aureus, Haemophilus pittmaniae, Romboutsia timonensis, Turicibacter sanguinis*, and *Turicibacter* sp. H121, and the plurality of KEGG ortholog definitions includes at least 20 KEGG ortholog definitions selected from ferredoxin-nitrite reductase, cytochrome c-type biogenesis protein Ccmf, methylaspartate ammonia-lyase, AraC family transcriptional regulator, small subunit ribosomal protein S20, oleate hydratase, small subunit ribosomal protein S16, type III restriction enzyme, tyrosine phenol-lyase, large subunit ribosomal protein L19, CDP-4-dehydro-6-deoxyglucose reductase E1, peroxiredoxin 2/4, L-ascorbate 6-phosphate lactonase, starvation-inducible DNA-binding protein, spore protease, serine/threonine-protein kinase HipA, methanol-5-hydroxybenzimidazolylcobamide co-methyltransferase, opine dehydrogenase, ferrous iron transport protein A, beta-glucosidase, molecular chaperone IbpB, dihydrofolate reductase, glycerol-3-phosphate dehydrogenase subunit B, two-component system OmpR family phosphate regulon response regulator OmpR, putative transposase, fructoselysine 6-phosphate deglycase, propionyl CoA carboxylase beta chain, OmpA-OmpF porin OOP family, F-type H+ transporting ATPase subunit B, iron complex transport system substrate-binding protein, translocator protein, accessory gene regulator B, RNA polymerase sigma 70 factor ECF subfamily, anaerobic dimethyl sulfoxide reductase subunit B, putative ABC transport system ATP-binding protein, D-proline reductase (dithiol) stabilizing protein PrdE, fructoselysine 4-epimerase, stage V sporulation protein AC, glutamate synthase (NADPH) large chain, 6-phosphogluconate dehydrogenase, aryl-sulfate sulfotransferase, sirohydrochlorin cobaltochelatase, superoxide dismutase Fe—Mn family, glutamate decarboxylase, F-type H+/Na+ transporting ATPase subunit beta, actin, mRNA interferase MazF, and HSP20 family protein.

14. The method of claim 1, wherein the plurality of microbial taxa comprises *Streptococcus gordonii, Propionibacterium acidifaciens, Streptococcus mutans, Olsenella profuse, Streptococcus vestibularis, Alloscardovia omnicolens, Clostridium phoceensis, Massilioclostridium coli,* Ruminococcaceae bacterium Marseille-P2963, *Bifidobacterium dentium, Ruminococcus gauvreauii, Roseburia intestinalis, Streptococcus* sp. HMSC10A01, *Ruminococcus* sp. AT10, *Veillonella atypica, Turicibacter* sp. HGF1, *Olsenella uli, Penicillium digitatum, Pseudomonas aeruginosa, Intestinimonas butyriciproducens, Ruminoccocus* sp. Marseille-P3213, *Streptococcus* sp. CCH8-G7, Lachnospiraceae bacterium TF01-11, *Bifidobacterium* sp. MSTE12, *Pseudoflavonifractor capillosus, Streptococcus parasanguinis,* Clostridia bacterium UC5 1-1E11, *Subdoligranulum* sp 4_3_54A2FAA, *Corynebacterium matruchotii, Actinomyces dentalis,* Actinomycetaceae bacterium BA112, *Bacteroides* sp. HPS0048, *Butyricicoccus pullicaecorum, Rothia mucilaginosa, Parascardovia denticolens, Dialister invisus, Faecalibacterium prausnitzii,* Tobacco mild green mosaic virus, *Peptostreptococcus stomatis, Atopobium* sp. HMSC064B08, *Clostridiales* bacterium, *Ruminococcus faecis, Atopobium rimae, Actinomyces* sp. oral taxon 181, *Streptococcus intermedius, Parasutterella excrementihominis, Sutterella wadsworthensis, Lactobacillus iners, Urmitella timonensis, Abiotrophia* sp. HMSC24B09, *Hungatella hathewayi, Ruminococcus* sp. DSM 100440, *Streptococcus* sp. F0442, *Coprococcus eutactus, Haemophilus sputorum, Actinomyces gerencseriae, Catabacter hongkongensis, Gemella morbillorum, Clostridium ventriculi, Eubacterium* sp. 3_1_31, *Lactobacillus crispatus, Bifidobacterium longum, Campylobacter hominis, Streptococcus anginosus, Shewanella colwelliana, Staphylococcus aureus, Haemophilus pittmaniae, Romboutsia timonensis, Turicibacter sanguinis*, and *Turicibacter* sp. H121, and the plurality of KEGG ortholog definitions includes ferredoxin-nitrite reductase, cytochrome c-type biogenesis protein Ccmf, methylaspartate ammonia-lyase, AraC family transcriptional regulator, small subunit ribosomal protein S20, oleate hydratase, small subunit ribosomal protein S16, type III restriction enzyme, tyrosine phenol-lyase, large subunit ribosomal protein L19, CDP-4-dehydro-6-deoxyglucose reductase E1, peroxiredoxin 2/4, L-ascorbate 6-phosphate lactonase, starvation-inducible DNA-binding protein, spore protease, serine/threonine-protein kinase HipA, methanol-5-hydroxybenzimidazolylcobamide co-methyltransferase, opine dehydrogenase, ferrous iron transport protein A, beta-glucosidase, molecular chaperone IbpB, dihydrofolate reductase, glycerol-3-phosphate dehydrogenase subunit B, two-component system OmpR family phosphate regulon response regulator OmpR, putative transposase, fructoselysine 6-phosphate deglycase, propionyl CoA carboxylase beta chain, OmpA-OmpF porin OOP family, F-type H+ transporting ATPase subunit B, iron complex transport system substrate-binding protein, translocator protein, accessory gene regulator B, RNA polymerase sigma 70 factor ECF subfamily, anaerobic dimethyl sulfoxide reductase subunit B, putative ABC transport system ATP-binding protein, D-proline reductase (dithiol) stabilizing protein PrdE, fructoselysine 4-epimerase, stage V sporulation protein AC, glutamate synthase (NADPH) large chain, 6-phosphogluconate dehydrogenase, aryl-sulfate sulfotransferase, sirohydrochlorin cobaltochelatase, superoxide dismutase Fe—Mn family, glutamate decarboxylase, F-type H+/Na+ transporting ATPase subunit beta, actin, mRNA interferase MazF, and HSP20 family protein.

15. The method of claim 1, wherein the plurality of microbial taxa comprises at least two of *Streptococcus gordonii, Propionibacterium acidifaciens, Streptococcus mutans, Turicibacter* sp. H121, *Turicibacter sanguinis, Olsenella profuse, Romboutsia timonensis, Haemophilus pittmaniae, Streptococcus vestibularis*, and *Alloscardovia omnicolens*.

16. The method of claim 1, wherein the plurality of microbial taxa comprises at least three of *Streptococcus gordonii, Propionibacterium acidifaciens, Streptococcus mutans, Turicibacter* sp. H121, *Turicibacter sanguinis, Olsenella profuse, Romboutsia timonensis, Haemophilus pittmaniae, Streptococcus vestibularis*, and *Alloscardovia omnicolens*.

17. A computer system comprising:
one or more processors;
memory; and
one or more programs, wherein the one or more programs are stored in the memory and configured to be executed by the one or more processors, the one or more programs including instructions for performing a method for inferring biological age in a subject comprising:
a) obtaining first sequence information in electronic form for a first plurality of nucleic acids, wherein the first plurality of nucleic acids comprises 10,000 or more sequences representing a microbiome of a subject, and wherein the first plurality of nucleic acids are from a first biological sample of the subject;
b) determining, from the first sequence information, a respective measure of transcriptional activity for each respective microbial taxa in a plurality of microbial taxa, wherein:
the plurality of microbial taxa comprises at least 5 taxa selected from *Streptococcus gordonii*, *Propionibacterium acidifaciens*, *Streptococcus mutans*, *Olsenella profuse*, *Streptococcus vestibularis*, *Alloscardovia omnicolens*, *Clostridium phoceensis*, *Massilioclostridium coli*, Ruminococcaceae bacterium Marseille-P2963, *Bifidobacterium dentium*, *Ruminococcus gauvreauii*, *Roseburia intestinalis*, *Streptococcus* sp. HMSC10A01, *Ruminococcus* sp. AT10, *Veillonella atypica*, *Turicibacter* sp. HGF1, *Olsenella uli*, *Penicillium digitatum*, *Pseudomonas aeruginosa*, *Intestinimonas butyriciproducens*, *Ruminoccocus* sp. Marseille-P3213, *Streptococcus* sp. CCH8-G7, Lachnospiraceae bacterium TF01-11, *Bifidobacterium* sp. MSTE12, *Pseudoflavonifractor capillosus*, *Streptococcus parasanguinis*, *Clostridia bacterium* UC5 1-1E11, *Subdoligranulum* sp 4_3_54A2FAA, *Corynebacterium matruchotii*, *Actinomyces dentalis*, Actinomycetaceae bacterium BA112, *Bacteroides* sp. HPS0048, *Butyricicoccus pullicaecorum*, *Rothia mucilaginosa*, *Parascardovia denticolens*, *Dialister invisus*, *Faecalibacterium prausnitzii*, Tobacco mild green mosaic virus, *Peptostreptococcus stomatis*, *Atopobium* sp. HMSC064B08, *Clostridiales bacterium*, *Ruminococcus faecis*, *Atopobium rimae*, *Actinomyces* sp. oral taxon 181, *Streptococcus intermedius*, *Parasutterella excrementihominis*, *Sutterella wadsworthensis*, *Lactobacillus iners*, *Urmitella timonensis*, *Abiotrophia* sp. HMSC24B09, *Hungatella hathewayi*, *Ruminococcus* sp. DSM 100440, *Streptococcus* sp. F0442, *Coprococcus eutactus*, *Haemophilus sputorum*, *Actinomyces gerencseriae*, *Catabacter hongkongensis*, *Gemella morbillorum*, *Clostridium ventriculi*, *Eubacterium* sp. 3_1_31, *Lactobacillus crispatus*, *Bifidobacterium longum*, *Campylobacter hominis*, *Streptococcus anginosus*, *Shewanella colwelliana*, *Staphylococcus aureus*, *Haemophilus pittmaniae*, *Romboutsia timonensis*, *Turicibacter sanguinis*, and *Turicibacter* sp. H121, and
the respective measure is obtained by matching each respective nucleic acid in the first plurality of nucleic acids to individual sequences of the plurality of taxa;
c) obtaining second sequence information in electronic form for a second plurality of nucleic acids, wherein the second plurality of nucleic acids comprises 10,000 or more sequences representing a transcriptome of the subject, and wherein the second plurality of nucleic acids are from a second biological sample of the subject;
d) determining, from the second sequence information, a respective measure of transcriptional activity for each respective KEGG ortholog definition in a plurality of KEGG ortholog definitions as an abundance of nucleic acids encoding the respective KEGG ortholog, wherein:
the plurality of KEGG ortholog definitions includes at least 5 KEGG ortholog definitions selected from ferredoxin-nitrite reductase, cytochrome c-type biogenesis protein Ccmf, methylaspartate ammonia-lyase, AraC family transcriptional regulator, small subunit ribosomal protein S20, oleate hydratase, small subunit ribosomal protein S16, type III restriction enzyme, tyrosine phenol-lyase, large subunit ribosomal protein L19, CDP-4-dehydro-6-deoxyglucose reductase E1, peroxiredoxin 2/4, L-ascorbate 6-phosphate lactonase, starvation-inducible DNA-binding protein, spore protease, serine/threonine-protein kinase HipA, methanol-5-hydroxybenzimidazolylcobamide co-methyltransferase, opine dehydrogenase, ferrous iron transport protein A, beta-glucosidase, molecular chaperone IbpB, dihydrofolate reductase, glycerol-3-phosphate dehydrogenase subunit B, two-component system OmpR family phosphate regulon response regulator OmpR, putative transposase, fructoselysine 6-phosphate deglycase, propionyl CoA carboxylase beta chain, OmpA-OmpF porin OOP family, F-type H+ transporting ATPase subunit B, iron complex transport system substrate-binding protein, translocator protein, accessory gene regulator B, RNA polymerase sigma 70 factor ECF subfamily, anaerobic dimethyl sulfoxide reductase subunit B, putative ABC transport system ATP-binding protein, D-proline reductase (dithiol) stabilizing protein PrdE, fructoselysine 4-epimerase, stage V sporulation protein AC, glutamate synthase (NADPH) large chain, 6-phosphogluconate dehydrogenase, aryl-sulfate sulfotransferase, sirohydrochlorin cobaltochelatase, superoxide dismutase Fe—Mn family, glutamate decarboxylase, F-type H+/Na+ transporting ATPase subunit beta, actin, mRNA interferase MazF, and HSP20 family protein, and
the respective measure is obtained by matching each respective nucleic acid in the second plurality of nucleic acids to individual sequences of the plurality of KEGG ortholog definitions; and
e) inputting into a model (i) the respective measure of transcriptional activity for each respective microbial taxa in the plurality of microbial taxa and (ii) the respective measure of transcriptional activity for each respective KEGG ortholog definition in the plurality of KEGG ortholog definitions, to obtain as output from the model a biological age of the subject.

18. A non-transitory computer readable storage medium storing one or more programs, the one or more programs comprising instructions, which when executed by an electronic device with one or more processors and a memory cause the electronic device to perform a method for inferring biological age in a subject comprising:
a) obtaining first sequence information in electronic form for a first plurality of nucleic acids, wherein the first plurality of nucleic acids comprises 10,000 or more sequences representing a microbiome of a subject, and wherein the first plurality of nucleic acids are from a first biological sample of the subject;

b) determining, from the first sequence information, a respective measure of transcriptional activity for each respective microbial taxa in a plurality of microbial taxa, wherein:

the plurality of microbial taxa comprises at least 5 taxa selected from *Streptococcus gordonii, Propionibacterium acidifaciens, Streptococcus mutans, Olsenella profusa, Streptococcus vestibularis, Alloscardovia omnicolens, Clostridium phoceensis, Massilioclostridium coli,* Ruminococcaceae bacterium Marseille-P2963, *Bifidobacterium dentium, Ruminococcus gauvreauii, Roseburia intestinalis, Streptococcus* sp. HMSC10A01, *Ruminococcus* sp. AT10, *Veillonella atypica, Turicibacter* sp. HGF1, *Olsenella uli, Penicillium digitatum, Pseudomonas aeruginosa, Intestinimonas butyriciproducens, Ruminoccoccus* sp. Marseille-P3213, *Streptococcus* sp. CCH8-G7, Lachnospiraceae bacterium TF01-11, *Bifidobacterium* sp. MSTE12, *Pseudoflavonifractor capillosus, Streptococcus parasanguinis,* Clostridia bacterium UC5 1-1E11, *Subdoligranulum* sp 4_3_54A2FAA, *Corynebacterium matruchotii, Actinomyces dentalis,* Actinomycetaceae bacterium BA112, *Bacteroides* sp. HPS0048, *Butyricicoccus pullicaecorum, Rothia mucilaginosa, Parascardovia denticolens, Dialister invisus, Faecalibacterium prausnitzii,* Tobacco mild green mosaic virus, *Peptostreptococcus stomatis, Atopobium* sp. HMSC064B08, *Clostridiales* bacterium, *Ruminococcus faecis, Atopobium rimae, Actinomyces* sp. oral taxon 181, *Streptococcus intermedius, Parasutterella excrementihominis, Sutterella wadsworthensis, Lactobacillus iners, Urmitella timonensis, Abiotrophia* sp. HMSC24B09, *Hungatella hathewayi, Ruminococcus* sp. DSM 100440, *Streptococcus* sp. F0442, *Coprococcus eutactus, Haemophilus sputorum, Actinomyces gerencseriae, Catabacter hongkongensis, Gemella morbillorum, Clostridium ventriculi, Eubacterium* sp. 3_1_31, *Lactobacillus crispatus, Bifidobacterium longum, Campylobacter hominis, Streptococcus anginosus, Shewanella colwelliana, Staphylococcus aureus, Haemophilus pittmaniae, Romboutsia timonensis, Turicibacter sanguinis,* and *Turicibacter* sp. H121, and the respective measure is obtained by matching each respective nucleic acid in the first plurality of nucleic acids to individual sequences of the plurality of taxa;

c) obtaining second sequence information in electronic form for a second plurality of nucleic acids, wherein the second plurality of nucleic acids comprises 10,000 or more sequences representing a transcriptome of the subject, and wherein the second plurality of nucleic acids are from a second biological sample of the subject;

d) determining, from the second sequence information, a respective measure of transcriptional activity for each respective KEGG ortholog definition in a plurality of KEGG ortholog definitions as an abundance of nucleic acids encoding the respective KEGG ortholog, wherein:

the plurality of KEGG ortholog definitions includes at least 5 KEGG ortholog definitions selected from ferredoxin-nitrite reductase, cytochrome c-type biogenesis protein Ccmf, methylaspartate ammonialyase, AraC family transcriptional regulator, small subunit ribosomal protein S20, oleate hydratase, small subunit ribosomal protein S16, type III restriction enzyme, tyrosine phenol-lyase, large subunit ribosomal protein L19, CDP-4-dehydro-6-deoxyglucose reductase E1, peroxiredoxin 2/4, L-ascorbate 6-phosphate lactonase, starvation-inducible DNA-binding protein, spore protease, serine/threonine-protein kinase HipA, methanol-5-hydroxybenzimidazolylcobamide co-methyltransferase, opine dehydrogenase, ferrous iron transport protein A, beta-glucosidase, molecular chaperone IbpB, dihydrofolate reductase, glycerol-3-phosphate dehydrogenase subunit B, two-component system OmpR family phosphate regulon response regulator OmpR, putative transposase, fructoselysine 6-phosphate deglycase, propionyl CoA carboxylase beta chain, OmpA-OmpF porin OOP family, F-type H+ transporting ATPase subunit B, iron complex transport system substrate-binding protein, translocator protein, accessory gene regulator B, RNA polymerase sigma 70 factor ECF subfamily, anaerobic dimethyl sulfoxide reductase subunit B, putative ABC transport system ATP-binding protein, D-proline reductase (dithiol) stabilizing protein PrdE, fructoselysine 4-epimerase, stage V sporulation protein AC, glutamate synthase (NADPH) large chain, 6-phosphogluconate dehydrogenase, aryl-sulfate sulfotransferase, sirohydrochlorin cobaltochelatase, superoxide dismutase Fe—Mn family, glutamate decarboxylase, F-type H+/Na+ transporting ATPase subunit beta, actin, mRNA interferase MazF, and HSP20 family protein, and the respective measure is obtained by matching each respective nucleic acid in the second plurality of nucleic acids to individual sequences of the plurality of KEGG ortholog definitions; and e) inputting into a model (i) the respective measure of transcriptional activity for each respective microbial taxa in the plurality of microbial taxa and (ii) the respective measure of transcriptional activity for each respective KEGG ortholog definition in the plurality of KEGG ortholog definitions, to obtain as output from the model a biological age of the subject.

\* \* \* \* \*